(12) United States Patent
Wang et al.

(10) Patent No.: US 11,885,798 B2
(45) Date of Patent: Jan. 30, 2024

(54) CENTRIFUGE AND METHOD FOR LOADING AND CENTRIFUGING A REACTION VESSEL UNIT

(71) Applicant: Yantai AusBio Laboratories Co., Ltd., Shandong (CN)

(72) Inventors: Zhaoqiang Wang, Yantai (CN);
Wolfgang Mann, Neudrossenfeld (DE);
Wolfgang Heimberg, Ebersberg (DE)

(73) Assignee: YANTAI AUSBIO LABORATORIES CO., LTD., Yantai (CN)

( * ) Notice: Subject to any disclaimer, the term of this patent is extended or adjusted under 35 U.S.C. 154(b) by 747 days.

(21) Appl. No.: 16/243,644

(22) Filed: Jan. 9, 2019

(65) Prior Publication Data

US 2019/0145968 A1   May 16, 2019

Related U.S. Application Data

(63) Continuation of application No. 14/910,681, filed as application No. PCT/EP2014/066947 on Aug. 6, 2014, now Pat. No. 10,338,063.

(30) Foreign Application Priority Data

Aug. 6, 2013 (EP) .................................. 13179437

(51) Int. Cl.
*G01N 33/543*   (2006.01)
*B08B 3/10*   (2006.01)
(Continued)

(52) U.S. Cl.
CPC ........ *G01N 33/54326* (2013.01); *B01L 9/523* (2013.01); *B01L 13/02* (2019.08);
(Continued)

(58) Field of Classification Search
CPC ....... G01N 33/54326; G01N 33/54366; G01N 35/028; G01N 2035/0437; B01L 13/02;
(Continued)

(56) References Cited

U.S. PATENT DOCUMENTS

| 2,561,186 A | 7/1951 | Dunham |
| 3,116,626 A | 1/1964 | Moschetti |

(Continued)

FOREIGN PATENT DOCUMENTS

| CN | 2147902 Y | 12/1993 |
| CN | 2197666 Y | 5/1995 |

(Continued)

OTHER PUBLICATIONS

Japanese Patent Application 2016-532683 Office Action dated Sep. 11, 2017.

(Continued)

*Primary Examiner* — Walter D. Griffin
*Assistant Examiner* — Shuyi S. Liu
(74) *Attorney, Agent, or Firm* — Jason M. Shapiro; Devlin Law Firm LLC

(57) ABSTRACT

A centrifuge for cleaning a reaction vessel unit, having a rotor for holding at least one reaction vessel unit with its opening(s) directed outwardly, a motor for rotating the rotor around a rotation axis, and a loading mechanism with a beam for loading and unloading the centrifuge with the at least one reaction vessel unit.

22 Claims, 18 Drawing Sheets

Figure 1:
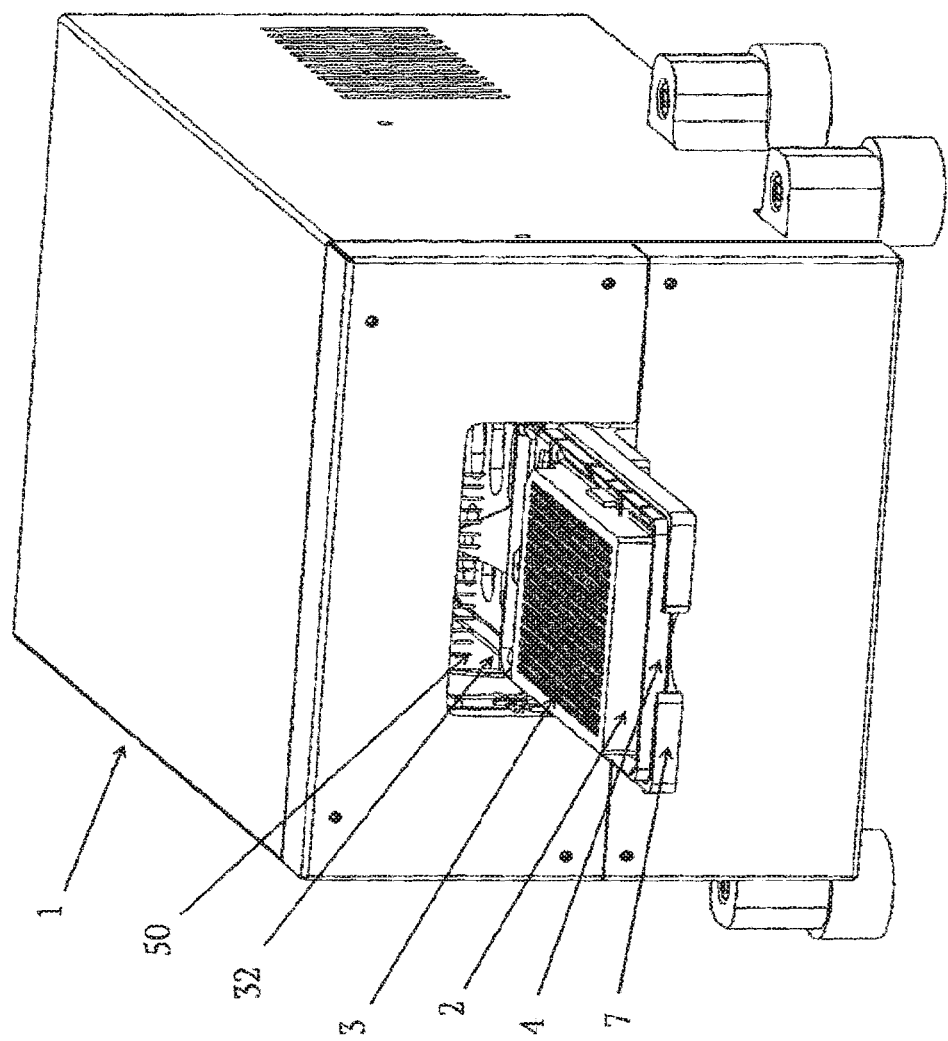

(51) Int. Cl.

| | | |
|---|---|---|
| *B08B 9/00* | (2006.01) | |
| *B04B 5/04* | (2006.01) | |
| *G01N 35/02* | (2006.01) | |
| *B03C 1/00* | (2006.01) | |
| *B03C 1/01* | (2006.01) | |
| *B03C 1/28* | (2006.01) | |
| *B03C 1/30* | (2006.01) | |
| *B04B 7/04* | (2006.01) | |
| *B01L 9/00* | (2006.01) | |
| *B08B 3/04* | (2006.01) | |
| *B08B 3/06* | (2006.01) | |
| *B04B 11/04* | (2006.01) | |
| *B04B 15/02* | (2006.01) | |
| *B08B 3/02* | (2006.01) | |
| *G01N 35/04* | (2006.01) | |
| *B01L 3/00* | (2006.01) | |

(52) U.S. Cl.
CPC ............... *B03C 1/002* (2013.01); *B03C 1/01* (2013.01); *B03C 1/288* (2013.01); *B03C 1/30* (2013.01); *B04B 5/0407* (2013.01); *B04B 5/0414* (2013.01); *B04B 7/04* (2013.01); *B04B 15/02* (2013.01); *B08B 3/02* (2013.01); *B08B 3/04* (2013.01); *B08B 3/06* (2013.01); *B08B 3/10* (2013.01); *B08B 9/00* (2013.01); *G01N 33/54366* (2013.01); *G01N 35/028* (2013.01); *B01L 3/5085* (2013.01); *B01L 2300/0829* (2013.01); *B01L 2400/0409* (2013.01); *B03C 2201/18* (2013.01); *B03C 2201/26* (2013.01); *B04B 2011/046* (2013.01); *G01N 2035/0437* (2013.01)

(58) Field of Classification Search
CPC ............... B01L 9/523; B01L 3/5085; B01L 2300/0829; B01L 2400/0409; B08B 3/02; B08B 3/04; B08B 3/06; B08B 3/10; B08B 9/00; B04B 7/04; B04B 15/02; B04B 5/0407; B04B 5/0414; B04B 2011/046; B04B 5/00; B03C 1/002; B03C 1/01; B03C 1/288; B03C 1/30; B03C 2201/18; B03C 2201/26
USPC ............... 506/3; 134/157, 180; 422/533; 436/526; 494/16, 20
See application file for complete search history.

(56) References Cited

U.S. PATENT DOCUMENTS

| | | | |
|---|---|---|---|
| 3,951,334 A | 4/1976 | Fleming et al. | |
| 4,236,666 A | 12/1980 | Aeschlimann | |
| 4,931,385 A | 6/1990 | Block et al. | |
| 4,953,575 A | 9/1990 | Tervamaki | |
| 5,419,871 A | 5/1995 | Muszak et al. | |
| 5,779,907 A | 7/1998 | Yu | |
| 6,112,603 A * | 9/2000 | Pietila | B01L 3/0203 73/863.23 |
| 6,150,182 A | 11/2000 | Cassaday et al. | |
| 6,502,877 B2 * | 1/2003 | Schick | B25J 15/06 294/185 |
| 6,929,596 B2 | 8/2005 | Amirkhanian | |
| 7,510,687 B2 | 3/2009 | Mazzeo et al. | |
| 8,329,475 B2 | 12/2012 | Jacobs et al. | |
| 8,973,736 B2 * | 3/2015 | Johns | B01D 21/262 198/439 |
| 9,492,828 B2 * | 11/2016 | Nichols | B04B 7/02 |
| 10,928,387 B2 | 2/2021 | Wang et al. | |
| 2004/0087426 A1 * | 5/2004 | Lattanzi | B04B 5/0421 494/20 |
| 2004/0208790 A1 | 10/2004 | Daf | |
| 2006/0142134 A1 | 6/2006 | Andersson et al. | |
| 2006/0198759 A1 | 9/2006 | Shneider | |
| 2009/0117620 A1 | 5/2009 | Fritchie et al. | |
| 2009/0181359 A1 | 7/2009 | Lou et al. | |
| 2012/0171941 A1 | 7/2012 | Matsuzawa | |
| 2012/0308435 A1 * | 12/2012 | Fritchie | B04B 9/146 422/73 |
| 2013/0065771 A1 | 3/2013 | Oroskar | |
| 2013/0152971 A1 | 6/2013 | Kato | |
| 2019/0145969 A1 | 5/2019 | Wang et al. | |
| 2021/0270826 A1 | 9/2021 | Wang et al. | |

FOREIGN PATENT DOCUMENTS

| | | |
|---|---|---|
| CN | 2565547 Y | 8/2003 |
| CN | 101284259 A | 10/2008 |
| CN | 102175855 A | 9/2011 |
| CN | 102417902 A | 4/2012 |
| DE | 102008007889 A1 | 1/2009 |
| DE | 102008042971 A1 | 4/2010 |
| DE | 102004012025 C5 | 4/2012 |
| DE | 202012001679 U1 | 5/2012 |
| EP | 0937502 A2 | 8/1999 |
| EP | 1952890 A2 | 8/2008 |
| EP | 2749356 A2 | 7/2014 |
| IT | TO20110009 A1 | 1/2011 |
| JP | S47-40437 | 10/1972 |
| JP | S47040437 | 10/1972 |
| JP | S5143967 | 3/1976 |
| JP | S55-031427 | 8/1980 |
| JP | H08160051 A | 6/1996 |
| JP | 2003010647 A | 1/2003 |
| JP | 2005081281 A | 3/2005 |
| JP | 2007-178355 A | 7/2007 |
| JP | 2009079940 A | 4/2009 |
| JP | 2009156717 A | 7/2009 |
| JP | 2009264927 A | 11/2009 |
| JP | 2009271069 A | 11/2009 |
| JP | 20090264927 A | 11/2009 |
| JP | 2010274230 A | 12/2010 |
| JP | 2011013042 A | 1/2011 |
| JP | 2012134390 A | 7/2012 |
| JP | S57-35854 | 12/2012 |
| WO | 9310455 | 5/1993 |
| WO | 00/00302 A1 | 1/2000 |

OTHER PUBLICATIONS

Micronix, "Specifications for the Product—Gyrowasher," 5 pages, dated Jul. 2011 (publication date unknown).

Micronix, "Gyrowasher Passage Drawing," 1 page, dated Apr. 2011 (publication date unknown).

Decision for Final Rejection for JP Patent Application No. 2016-532683 dated Apr. 20, 2018, 6 pages.

EP 13179437.2, European Search Report, dated Apr. 16, 2014, pp. 1-17.

MagMax Express 96 User Manual, Rev. 1.5, Jun. 2008, pp. 1-73, Applied Biosystems, USA.

Immunoprecipitation, Aug. 2, 2013, pp. 1-7, Wikipedia, Web source.

International Search Report PCT/EP2014/066947, search dated Feb. 25, 2015, pp. 1-9.

Written Opinion of the ISA PCT/EP2014/066947, dated Mar. 26, 2015, pp. 1-18.

State Intellectual Property Office of People's Republic of China, Office Action, dated Nov. 3, 2016, Issue Ser. No. 201610310100548 0, Beijing, China.

"Gyro Washer GW-384" and photographs, submitted as Exhibit D12 in cancellation proceeding for German Utility Patent No. DE202014010544U1 on Nov. 28, 2018, publication date unknown, 39 pages.

Japanese Preliminary Notice of Reasons for Rejection in Japanese Patent Application No. 2018-164143, dated May 28, 2019, 23 pages with English translation.

Preliminary Notice of Reasons for Rejection received in related Japanese Application No. 2018-164143, with English translation, dated Dec. 10, 2019 (7 pages.).

(56) References Cited

OTHER PUBLICATIONS

Institution Decision in Case No. PGR2020-00051 for U.S. Pat. No. 10,338,063, dated Dec. 15, 2020 (42 pages).
Request for Rehearing in PGR2020-00051 for U.S. Pat. No. 10,338,063, dated Dec. 29, 2020 (25 pages).
Photograph of Gyro Washer engineering drawing circling "vacuum pump" and "waste liquid option" dated Apr. 22, 2011, 1 page.
Decision Rejecting the Opposition in related EP App. No. 14753044. 8, European Patent 3030353, dated Jan. 2, 2020, 70 pages with application.
Petition for Post Grant Review of U.S. Pat. No. 10,338,063, Case No. PGR2020-00051, dated Apr. 1, 2020 (129 pages).
Exhibit 1017 from PGR2020-00051, "Gyro Washer GW-384," submitted Apr. 1, 2020 (81 pages).
Exhibit 1014 from PGR2020-00051, Statement of Delivery, submitted Apr. 1, 2020 (3 pages).
Exhibit 1003 from PGR2020-00051, "Specifications for the Product—Gyro Washer," submitted Apr. 1, 2020 (23 pages).
Exhibit 1004 from PGR2020-00051, "Gyro Washer," submitted Apr. 1, 2020 (10 pages).
Exhibit 1005 from PGR2020-00051, Declaration of Yoshiki Yagi, submitted Apr. 1, 2020 (96 pages).
Exhibit 1006 from PGR2020-00051, Declaration of Alexander H. Slocum, Ph D., submitted Apr. 1, 2020 (74 pages).
Exhibit 1007 from PGR2020-00051, Curriculum vitae of Alexander H. Slocum, submitted Apr. 1, 2020 (45 pages).
Exhibit 1008 from PGR2020-00051, Gyro Washer Brochure, submitted Apr. 1, 2020 (4 pages).
Exhibit 1009 from PGR2020-00051, Wako Pure Chemical Industries, Ltd. Brochure, submitted Apr. 1, 2020 (7 pages).
Exhibit 1010 from PGR2020-00051, Micronix Brochure, submitted Apr. 1, 2020 (4 pages).
Exhibit 1011 from PGR2020-00051, JP Pat. App. 2009-264927, submitted Apr. 1, 2020 (29 pages).
Exhibit 1013 from PGR2020-00051, "Gyro Washer Flow Diagram," submitted Apr. 1, 2020 (7 pages).
Notification of Grounds of Rejection received in Korean patent application No. 10-2016-7005920, dated Jul. 20, 2020 (21 pages).
Patent Owner Preliminary Response in PGR2020-00051, filed on Sep. 17, 2020 (101 pages).
Declaration of Dr. Joseph Katz in PGR2020-00051, filed on Sep. 17, 2020 (153 pages).
Statement of Delivery of Gyrowasher and Laptop PC from "C.A.N. Inc." to "Kyowa Hakko Kirin Co., Ltd" dated Aug. 30, 2011, 1 page.
Photograph of Gyro Washer binder, date unknown, 1 page.
Photograph of Gyro Washer design progress table, dated Apr. 7, 2011, 1 page.
Photograph of Gyro Washer engineering drawing circling "vacuum pump" and "waste liquid option," date unknown, 1 page.
"Experiment with GyroWasher," dated Jun. 25, 2019, 4 pages.
Claim Limitation chart for Micronix GyroWasher, date unknown, 8 pages.
Post Grant Review No. PGR2020-00051, Paper 64, Patent Owners Sur Reply, Filed Aug. 2, 2021.
Post Grant Review No. PGR2020-00051, Paper 58, Petitioner's Reply to Patent Owner's Response, Filed Jun. 15, 2021.
Post Grant Review No. PGR2020-00051, Exhibit 1039, Reply Declaration of Alexander Slocum, Filed Jun. 15, 2021.
Post Grant Review No. PGR2020-00051, Exhibit 1038, Yagi-san Reply Declaration, Filed Jun. 15, 2021.
Post Grant Review No. PGR2020-00051, Paper 53, Patent Owner Response, Filed Mar. 23, 2021.
Post Grant Review No. PGR2020-00051, Exhibit 2031, Second Declaration of Joseph Katz, Filed Mar. 23, 2021.
Post Grant Review No. PGR2020-00051, Exhibit 2035, Declaration of Paul Nisson, Filed Mar. 23, 2021.
Post Grant Review No. PGR2020-00051, Exhibit 2032, Gyro Washer Operating Manual, Filed Mar. 23, 2021.
Post Grant Review No. PGR2020-00051, Paper 26, Decision Granting Institution of Post-Grant Review, Filed Dec. 12, 2020.
Post Grant Review No. PGR2020-00051, Gyro Washer Inspection by Patent Owner, Screenshots from Videos taken Feb. 9, 2021.
International Preliminary Report issued in International Application No. PCT/EP2014/066947, dated Feb. 18, 2016, 20 pages.
Final Written Decision of Patent Trial and Appeal Board in PGR2020-00051 regarding U.S. Pat. No. 10,338,063, dated Dec. 9, 2021 (55 pages).
Office Action in related U.S. Appl. No. 17/151,999, dated May 10, 2023, 13 pages.

\* cited by examiner

CENTRIFUGE AND METHOD FOR LOADING AND CENTRIFUGING A REACTION VESSEL UNIT

CROSS-REFERENCE TO RELATED APPLICATIONS

This application is a continuation of non-provisional U.S. patent application Ser. No. 14/910,681, filed Feb. 5, 2016, entitled Centrifuge and Method for Centrifuging a Reaction Vessel Unit, which is a National Stage Entry of PCT/EP14/66947, filed Aug. 6, 2014, which claims priority to European Patent Application No. 13179437.2, filed Aug. 6, 2013, the contents of which are incorporated by reference herein in their entireties.

The present invention relates to a centrifuge and a method for centrifuging a reaction vessel unit.

US 2009/0181359 A1 discloses an automated immunoassay process having a high throughput and high sensitivity. As it is typical for immunoassay processes, a first specific binding member may react with a second specific binding member to form a complex wherein the concentration or the amount of the complex is determined. This process uses magnetic particles to which one of the specific binding members is immobilized. An important step in the automated process is washing the complex which is linked to the magnetic particles. The washing steps have a high impact on throughput sensitivity, specificity, and cost of the whole process. The less washing steps are needed, the faster the process is. The better the complexes are separated from non-specifically bound components the better is the sensitivity of the process.

U.S. Pat. No. 8,329,475 B2 discloses a wash process for removing undesired components in samples which are to be analyzed. Therein it is taught to oscillate the level of a wash fluid in a container. Such a container can be configured as a cup, well, cuvette, test tube, etc. By the oscillating process small amounts of wash fluid are dispensed and removed from the container. These amounts are smaller than the complete amount contained in the container. The oscillating action of the wash fluid creates a moving meniscus. The moving meniscus reduces the concentration gradient at the boundary layer of the container wall by constantly refreshing the wash fluid at the surface on the container wall.

Under the trade name SQUIRT™ a multi-format micro plate washer is available from the company matrical bioscience, USA. This washer comprises nozzles for squirting washing solution and air into the reaction vessels of microplates. Variable washing handles are provided. An automatic flipping element flips the micro plates so that a top-down washing is carried out. This microplate washer is compatible between different SBS/ANSI micro-well plate formats (96, 384, 1536, etc.).

Washing devices which wash by dispensing and aspirating the washing solution and/or air into and from reaction vessels cannot always remove successfully contaminating material that is present in the upper regions of the reaction vessels, as it is difficult to direct the jet of washing solution exactly adjacent to the upper boundary of the reaction vessel. Furthermore, there is a danger that the outer surface of the nozzles can be contaminated, particularly when a top-down washing step is carried out, wherein the nozzles are located below the reaction vessels. In the case of a typical human diagnostics test the starting material will be plasma or serum. Proteins present in such material tend to form complexes. Clogging of proteins and subsequent failure of aspiration is a major drawback in conventional washer systems. It leads to failure in automated systems and interruption of the total workflow in order to give chance for maintenance.

US 2009/0117620 A1 relates to a laboratory automation system that is capable of carrying out clinical chemistry assays, immunoassays, amplification of nucleic acid assays, and any combination of the foregoing. In this system, micro-well plates and deep multi-well plates are used as reaction vessels. The use of such multi-well plates allows carrying out immunoassays with a high throughput.

Other laboratory automation systems are using so called gel-cards instead of multi-well plates. The advantage of gel-cards in comparison to multi-well plates is that they can be automatically optically analyzed by scanning the side surfaces of the gel-cards. This allows implementing to analyze biological substances automatically by separating them in the gel column.

EP 937 502 A2 discloses a method for handling a microplate in which liquid is dosed into reaction vessels and the liquid is removed. After dosing the liquid into the reaction vessels the microplate is centrifuged so that the centrifugal force is exerted towards the bottom of the reaction vessels and then the sample plate is centrifuged so that the centrifugal force is exerted away from the bottom of the reaction vessels to empty the reaction vessels.

JP 2009-264927 A discloses a microplate treatment device comprising a rotating drum rotating around a horizontal rotation axis and having holding sections on a side surface of the rotating drum which each can hold a microplate. The drum is surrounded by a cover. The microplates can be placed in the drum so that the openings of the reaction vessels face to the outside or face to the inside of the drum.

From CN 102 175 855 A a washer for enzyme-labeled plates is known, comprising a rotating mechanism, a washing mechanism and a drainage mechanism. After the washing is completed, a centrifugal force, generated by continuous rotation, can throw off the water remaining in holes of the enzyme-labeled plates, so that a drying effect is realized, therefore the enzyme-level plates can be used at once after being washed.

U.S. Pat. No. 4,953,575 discloses a washing device for washing a cuvette set. The cuvette set is placed into a holder in a rotor. The cuvettes are filled with the washing liquid. The washing liquid is removed from the cuvettes by rotating the rotor.

The Italian patent application IT TO20 110 009 A relates to a centrifuge having a rotor. The rotor comprises an elastic cable and a small piston which is actuated by the elastic cable. The reaction vessels can be pushed out of corresponding receptions or cells during rotating of the rotor by means of the elastic cable and the small piston, wherein the reaction vessels are pushed in the direction to the rotation axis.

U.S. Pat. No. 5,419,871 pertains to an analyzer and an elevator for moving a slide element in a single horizontal plane, to one of plural incubators disposed at different vertical levels. A drive mechanism is provided for raising and lowering the elevator, and a pusher is provided such as a pusher blade within the elevator, to push a slide element from the distributor to a sup-port in the elevator, and then into one of the incubators.

U.S. Pat. No. 6,150,182 discloses a centrifuge for rotating a reaction vessel around a vertical axis. A magnetic element can be arranged in the vicinity of the reaction vessel so that the magnetic field supplied to the reaction vessel for holding the magnetic beads in the reaction vessel.

WO 93/10455 A1 relates to a centrifuge vessel for performing automated immunoassays comprising a center tube, an outer waste chamber, and a plurality of microparticle beads hosed within the center tube. The micro particle beads have a magnetizable core, which are acted upon an external magnetic source during washing operations.

From DE 10 2008 042 971 A1 a centrifuge is known for centrifuging a reaction vessel so that more heavy components are collected in the lower section of the reaction vessel. The lower section of the reaction vessel is surrounded by a magnetic element which holds magnetic beads for a while after centrifuging in the lower section of the reaction vessel.

CN 102 417 902 A relates to a kit for extracting nucleic acid by a magnetic bead-microtiterplate method.

US 2006/0198759 A1 discloses a centrifuge which can be used in a mixing mode for oscillating the rotor back and forth.

EP 1 952 890 A2 discloses a centrifuge adding a plurality of centrifuge disks. Each disk is embodied for attaching a gel-card and rotating the gel-card around a horizontal axis.

An object of the present invention is to provide a centrifuge for cleaning a reaction vessel unit.

This object is solved by the centrifuge procuring a reaction vessel unit as defined in claim 1.

Preferred embodiments are defined in the corresponding subclaims.

A centrifuge for cleaning a reaction vessel unit, having a rotor for holding at least one reaction vessel unit with its opening(s) directed outwardly, a motor for rotating the rotor around a rotation axis, a housing having preferably a substantially cylindrical inner surface, wherein a drain is provided for discharging fluid expelled from the reaction vessel unit, wherein a gap is provided between the inner surface and the rotor so that by rotating the rotor a wind is generated which drives the expelled fluid on the inner surface to the drain wherein an aspiration pump is connected to the drain for discharging fluid.

An aspiration pump connected to the drain of the centrifuge allows a faster and improved clearing of the housing. This is important for avoiding cross-contaminations based on sample liquid present on the walls and bottom of the housing of the centrifuge. By the connected aspiration pump the liquid discharged from the reaction vessel(s) is sucked immediately when the pump is switched on. The pump can either be running during the centrifugation or switched on at any point of time as desired. Any residual liquid remaining in the housing after switching off the aspiration pump can be removed manually. However, the main part will already be removed by the pump and thus, decreases the risk of any cross-contamination enormously.

A centrifuge for cleaning a reaction vessel unit comprises a rotor for holding at least one reaction vessel unit with its opening(s) directed radially outwardly, a motor for rotating the rotor around a rotation axis, a housing having a substantially cylindrical inner surface surrounding the rotor, wherein a drain is provided for discharging fluid expelled from the reaction vessel unit, wherein a gap of not more than 1 mm is provided between the cylindrical inner surface and the rotor, so that by rotating the rotor a wind or circular airstream is generated, which drives the expelled fluid on the cylindrical inner surface to the drain.

Due to the small gap between the rotor and the cylindrical inner surface a strong circular airstream is created by the rotating rotor, which drives the expelled fluid to the drain. Thus, it is possible to withdraw completely all liquid contained in the reaction vessel of the reaction vessel unit before rotating the rotor from the interior of the housing. This fluid is regarded as contaminating material. As this contaminating material can be completely be withdrawn, there is no danger of contamination. The gap is preferably not larger than 0.75 mm and particularly not larger than 0.5 mm. The smaller the gap the stronger is the circular airstream. However, this gap should preferably not be smaller than 0.1 mm and in particular not smaller than 0.2 mm or 0.3 mm, because such small gaps could cause the rotor to come into contact with the cylindrical inner surface.

A further object of the present invention is to provide a centrifuge for cleaning a reaction vessel unit which can reliably clean reaction vessel units containing volatile liquids.

This object is solved by a centrifuge for cleaning a reaction vessel according to claim 3. Preferred embodiments are defined in the corresponding subclaims.

A centrifuge for cleaning a reaction vessel unit comprises a rotor for holding at least one reaction vessel unit with its opening(s) directed radially outwardly, a motor for rotating the rotor around a rotation axis, and a housing.

A reaction vessel unit, such as a microtiter plate, can be cleaned or processed in that the reaction vessel unit is rotated, wherein the openings of the reaction vessels of the reaction vessel unit are directed radially outwardly. Thus, the liquid contained in the reaction vessels is expelled. If the liquid is a volatile liquid, then it is likely that a part of the liquid is vaporized.

This vaporized fluid can basically condense on a part of a reaction vessel unit and can cause a contamination.

For avoiding a contamination by condensation a cooling device is provided for cooling an inner surface of the housing so that a vaporized fluid is condensed on said inner surface and cannot condense on a reaction vessel unit. By cooling the inner surface it can be secured that volatile liquids are withdrawn from the gas atmosphere in the housing so that they can be completely discharged from the housing.

The cooling device for cooling the inner surface of the housing is preferably a Peltier element, particularly a Peltier foil, which covers the outer surface of the housing.

The inner surface of the housing is preferably kept cooler than at least 2° C. or 3° C. or at least even cooler than 5° C. than the other parts in the housing.

A further object of the present invention is to provide a centrifuge for centrifuging a reaction vessel unit which can be easily integrated in an automatic labor robot or can be easily coupled to an existing automatic labor robot.

This object is solved by a centrifuge according to claim 4. Advantageous embodiments are defined in the corresponding subclaims.

A centrifuge for centrifuging a reaction vessel unit comprises a rotor for holding at least one reaction vessel unit with its opening(s) directed radially outwardly and/or radially inwardly, a motor for rotating the rotor around a rotation axis, wherein the section in which the rotor is rotating forms a centrifuge section, a loading mechanism for loading and unloading the centrifuge with a reaction vessel unit, wherein the loading mechanism comprises a flexible elongated beam for extension and re-traction of a reaction vessel unit and a driving means for extending and retracting the beam, wherein the flexible elongate beam extends through the centrifuge section in its extended state and is removed from the centrifuge section in its retracted state so that the rotor can freely rotate.

This loading mechanism is rather simple and it can be integrated into the centrifuge needing only a small insulation space. This loading mechanism is embodied for horizontally moving a reaction vessel unit by extending or retracting the flexible elongated beam. Such a horizontal movement can be easily combined with known handling devices for automatic labor robots, because this loading mechanism extends into the moving range of the reaction vessel unit only horizontally so that it does not block the space above the moving range of the reaction vessel unit. This space can be completely be used by other parts of the centrifuge or the automatic labor robot. Other known handling means have usually parts being arranged above the moving range of a reaction vessel unit. Such parts could collide with other elements, particularly other handling means of an automatic labor robot.

The flexible elongated beam comprises preferably a magnetic coupling at its free end. Such a magnetic coupling can automatically couple to a reaction vessel unit or a reaction vessel unit carrier having a corresponding counter coupling element. Preferably, the rotor comprises a further magnetic coupling element which can hold the reaction vessel unit or the reaction vessel unit carrier by coupling the magnetic coupling of the rotor with the magnetic counter coupling element of the reaction vessel unit or the reaction vessel unit carrier.

The rotor comprises preferably a stopper for stopping the movement of the reaction vessel unit or the reaction vessel unit carrier when it is drawn into the rotor by means of the beam, so that the beam is automatically decoupled from the reaction vessel unit or the reaction vessel unit carrier, respectively.

The beam is preferably made of a bent metal sheet. The bent metal sheet is preferably bent into two strands or is winded-up on a reel.

The centrifuge according to any of the above described embodiments preferably comprises a tempering means for tempering the gas contained inside the housing and/or tempering the rotor. This tempering means can adjust the temperature in a range with a minimum value of 0° C., 10° C. or 20° C. and a maximum value of 40° C., 60° C. or 80° C. With such a tempering means an incubation step can be carried out without unloading the reaction vessel unit from the centrifuge. A suitable range of temperature has to be selected according to the kind of a biological or chemical reaction which is to be carried out.

The housing comprises preferably an automatic door for loading and unloading the reaction vessel unit, wherein the door is opened for moving the reaction vessel unit into or out of the interior of the housing or for exchanging the gas contained in the housing.

The centrifuge can be provided with a camera for scanning the reaction vessels of a reaction vessel unit. The camera can be placed with its field of vision directed to the bottom surfaces of the reaction vessels or to the side surfaces of the reaction vessels. The reaction vessel units, such as microtiter plates, comprising reaction vessels arranged in a two-dimensional area are preferably scanned at the bottom surfaces.

A reaction vessel unit comprising several reaction vessels arranged in parallel in line, such as a gel-card, comprises preferable reaction vessels which are colored on one side and the reaction vessels are made of a transparent material on the other side. The colored side improves the contrast when the reaction vessels are optically scanned at the transparent side.

The camera comprises preferably a light source, particularly a stroboscopic light source.

The above embodiments of the centrifuge are preferably embodied so that the rotor is rotating about a horizontal rotating axis or a rotating axis which is oriented parallel to a platform of the reaction vessel unit centrifuge, which is embodied for supporting the reaction vessel unit centrifuge in accordance with its designated use.

A further object of the present invention is to provide a multi-purpose centrifuge.

The object is solved by a centrifuge according to claim 13. Preferred embodiments are defined in the corresponding subclaims.

A centrifuge comprises a rotor for holding at least one reaction vessel unit with its opening(s) directed radially outwardly or radially inwardly, a motor for rotating the rotor around a rotation axis, a housing surrounding the rotor, wherein the housing comprises two openings for loading and unloading reaction vessel units, wherein the openings are arranged diametrically opposite with respect to the rotation axis.

Due to the two openings the centrifuge can be loaded with a reaction vessel unit, wherein the reaction vessels are directed with the openings radially outwardly or radially inwardly with respect to the rotation axis without the need of flipping the reaction vessel unit before loading into the centrifuge. Such a centrifuge can be used for cleaning and washing on one hand or centrifuging on the other hand. As there is no need for flipping the reaction vessel unit such a centrifuge can be easily integrated in an automatic labor robot and providing both functions.

According to a further independent aspect of the present invention a centrifuge is provided having
    a rotor for holding at least one reaction vessel unit with its opening(s) directed radially outwardly or radially inwardly with respect to the rotation axis,
    a motor for rotating the rotor around a rotation axis, and
    a control unit for controlling a movement of the rotor forth and back by a small angular distance of e.g. 5° to 20° for shaking the reaction vessel unit. Such a shaking process can be used for discharging the reaction vessels or for agitating the content in the reaction vessels for supporting chemical and/or biological reactions.

The above described embodiments of a centrifuge are preferably embodied so that the receptacle section is provided for holding a reaction vessel unit so that the reaction vessels are arranged substantially parallel to the rotation axis. Thus, merely the same centrifuge force is exerted to all the sample material. This applies for both a plurality of small reaction vessels which are arranged substantially parallel to the rotation axis as well as a large sample vessel such as a blood bag which comprises its main extension in the direction parallel to the rotation axis. Further examples of reaction vessels are channels, tubes, bottles. The reaction vessels can be arranged in microtiter plates, racks for carrying individual tubes or other carriers for taking-up any kind of vessel, such as a blood bag, or slides having structures for defining liquid spots thereon.

The receptacle section can be also embodied for holding a plurality of reaction vessels, wherein several reaction vessels are arranged in a substantially lateral direction to the rotation axis. This is for example the case in a microtiter plate, which comprises a plurality of rows with a large number of reaction vessels and a plurality of columns with a smaller number of reaction vessels. The rows are arranged parallel to the rotation axis, wherein the columns are extending lateral to the rotation axis. In such a case it is appropriate that the reaction vessel unit is arranged in a distance to the rotation axis which is substantially larger than the distance of the lateral extension of the reaction vessel unit. The distance between the rotation axis and the reaction vessel unit should be at least as large as the lateral extension and preferably at least 1.5, two times or three times as large as the lateral extension of the reaction vessel unit. With such an arrangement, it is also achieved that nearly the same centrifugal force is exerted on all the samples contained in the different reaction vessels. The lateral extension of the reaction vessel unit is the distance between the center of two laterally outmost reaction vessels.

A further advantage of a centrifuge with a horizontal rotation axis is that it needs only a small space of a platform in comparison to a centrifuge having a vertical rotation axis which is perpendicular to the platform.

Any of the above defined centrifuges can be combined with a dispensing device for automatically dispensing a fluid into the reaction vessels of a reaction vessel unit. Such a dispensing device is preferably located in the neighboring of an opening for inserting a reaction vessel unit into the centrifuge. The dispensing device can comprise one or more dispensing nozzles. Preferably the number of dispensing nozzles is adapted to the kind of reaction vessel unit which is used in the centrifuge. The dispensing device is connected to a reservoir for a dispensing solution, wherein a pump is provided for automatically pumping the dispensing solution to the dispensing nozzles. Preferably, a heating device is provided in the reservoir for dispensing solution for heating the dispensing solution.

The centrifuge comprises preferably and additionally a loading mechanism which is embodied so that the reaction vessel units are moved below the dispensing device, so that with one dispensing nozzle several reaction vessels which are arranged in line of the moving direction of the reaction vessel unit can be consecutively filled with a dispensing fluid.

For washing magnetic beads the rotor of a centrifuge for cleaning and washing reaction vessel units can be provided with a magnetic element applying a magnetic field to the reaction vessels, so that magnetic beads contained in the reaction vessels are hold in place by the magnetic field. The magnetic element can be integrated into the rotor, particularly in a base wall of the rotor, or can be part of a reaction vessel unit carrier. With such a magnetic element the magnetic beads can be washed by centrifugation without losing the magnetic beads. The combination of using a centrifuge for washing and using such a magnetic element allows adjusting the speed of rotation so that all magnetic beads are kept in the reaction vessels during centrifugation.

Furthermore, it is an object of the present invention to provide a method for emptying a reaction vessel by centrifugation.

This object is solved by a method, wherein a reaction vessel unit is placed in a rotor and, wherein the reaction vessel unit comprises at least one reaction vessel having an opening and the reaction vessel unit is placed with the opening of the reaction vessel radially outwardly for emptying the reaction vessel and the rotor is driven back and forth for shaking the reaction vessel unit.

After placing the at least one reaction vessel in the reaction vessel unit with the opening of the reaction vessel being placed radially outwardly, the method comprises preferably three steps. Firstly, the at least one reaction vessel is turned upside down by moving the rotor about 180 degrees. The reaction vessel is thereby moved from a topmost position in the centrifuge to a bottommost position. The speed for this half rotation is adjusted so that it is neither too slow nor too fast in order to prevent any spillovers between the vessels. In case of a too slow rotation speed sample liquid may pour from one vessel into another adjacent vessel.

In case of a too fast rotation speed the sample liquid will be ejected out of the vessels against the walls of the housing. Since at the beginning of the process the vessels are filled with a high volume of sample liquid the liquid ejected against the walls of the housing may splash back into the vessels or drop down into the vessels. However, by choosing the right speed for the half rotation, most of the sample liquid will basically fall out of the reaction vessel when turned upside down and can easily be collected on the bottom of the housing. To prevent any spillover effects the plate should be turned around with a preferred rotational speed of 0.2 to 1 second per 180 degrees.

In the second step the reaction vessel unit is shaken around the bottommost position by a control unit for controlling a movement of the rotor forth and back by a small angular distance of e.g. 5° to 20°. By this shaking process sample liquid, which did not fall out during the first rotational step, will be discharged from the reaction vessel.

The third step comprises the centrifugation of the reaction vessel unit at a high speed (e.g. between 500 to 3500 rpm) in order to remove all residual undesired sample liquid from the reaction vessel.

This method allows a quick and clear emptying of the reaction vessel without the risk of any spillover together with an easy collection of the discharged sample liquid. By only turning around the filled reaction vessel(s) for 180 degrees residual liquid will remain in the vessel due to capillary forces. The shaking of the vessel(s) around the bottommost position will help to overcome these forces and remove more of the sample liquid. However, even after the shaking step small amounts of liquid might be held back in the vessel. These minimal amounts will then be removed by the final step of actual centrifugation at high speeds for a longer time between 2 seconds up to 1 minute clockwise and/or counterclockwise. Thus, a completely dried reaction vessel will be obtained, whereby the liquid to be discharged is collected easily at the bottom of the housing of the centrifuge.

A further object of the present invention is to provide a method for parallel testing by means of gel separation, such as blood-typing, wherein a high throughput is achieved.

The object is solved by a method according to claim 15. The method comprises the following steps:
  dispensing sample material in the regions into reaction vessels arranged in a two dimensional array which are filled with gel,
  centrifuging the array of reaction vessels, and
  optical detecting the reaction vessels.

A microtiter plate comprises reaction vessels arranged in a two-dimensional area. Thus it is possible to simultaneously test a higher number of samples in comparison to reaction vessel units having only reaction vessels arranged in line.

The reaction vessels are optically detected, wherein it has been shown that an optical detection with the field of vision from below or from the top onto the reaction vessels of the array of reaction vessels (microtiter plate) allows to reliably detecting whether the expected result is achieved. This method was used for blood-typing, wherein automatically and reliably the blood types A, B and O could be detected and distinguished.

Preferably, the optical detection is carried out from both sides from below and from the top onto the array of reaction vessels.

Additionally it is possible to automatically prepare the microtiter plates for such testing by means of gel separation in that gel is filled into the reaction vessels of the microtiter plate, and the microtiter plate is centrifuged so that the gel becomes free of air bubbles.

The centrifugation steps of this method are preferably carried out with a centrifuge as defined above.

Instead of filling the reaction vessels with gel, also a microtiter plate can be used comprising already gel-filled reaction vessels.

After dispensing sample material and reagents into the reaction vessels onto the gel filling an incubation step can be carried out for keeping the microtiter plate for a certain period of time at a predetermined temperature. Most preferably the microtiter plate is kept in the centrifuge for carrying out this incubation step, wherein the centrifuge comprises a suitable tempering device. The centrifuge according to the invention can be used for numerous kinds of assays. Examples of possible assays are blood typing by means of microtiter plates, cellular assays, as-says comprising magnetic beads, or PCRs with an oil overlay to ensure the formation of two separate phases guaranteeing a full coverage of the vessel(s).

The present invention is a further development of the centrifuge according to PCT/EP2013/052356. PCT/EP2013/052356 is incorporated herein by reference.

Figure 2:
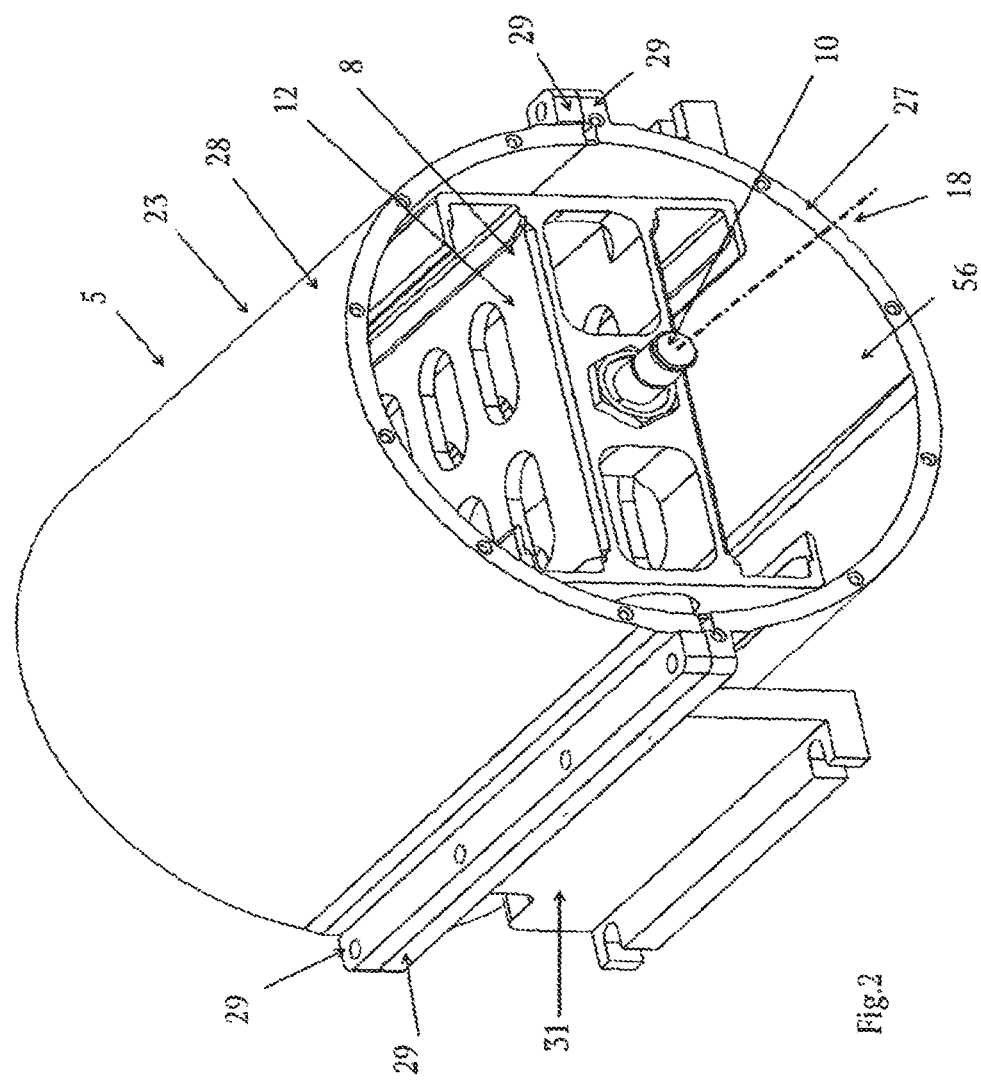
Figure 3:
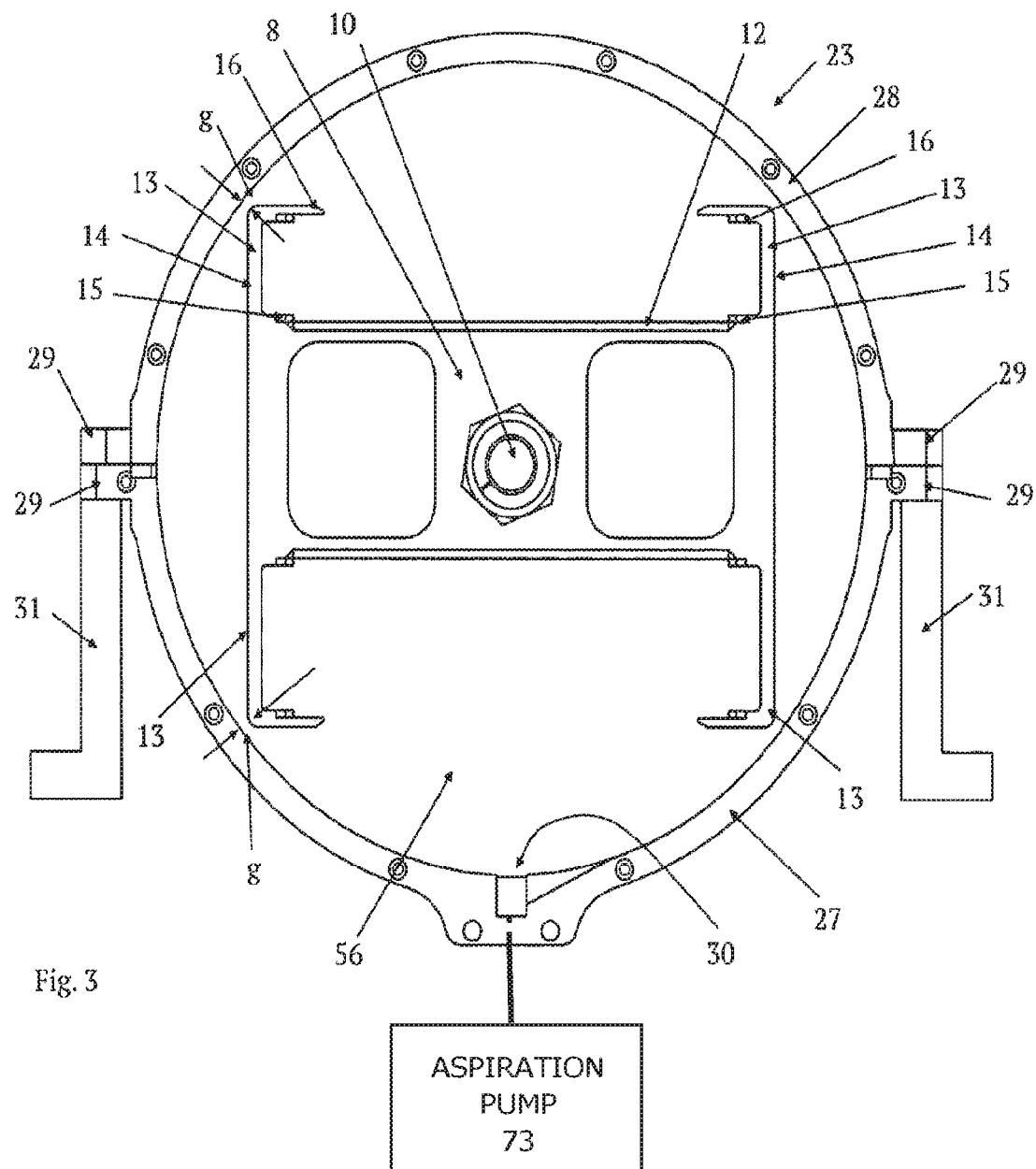
Figure 4:
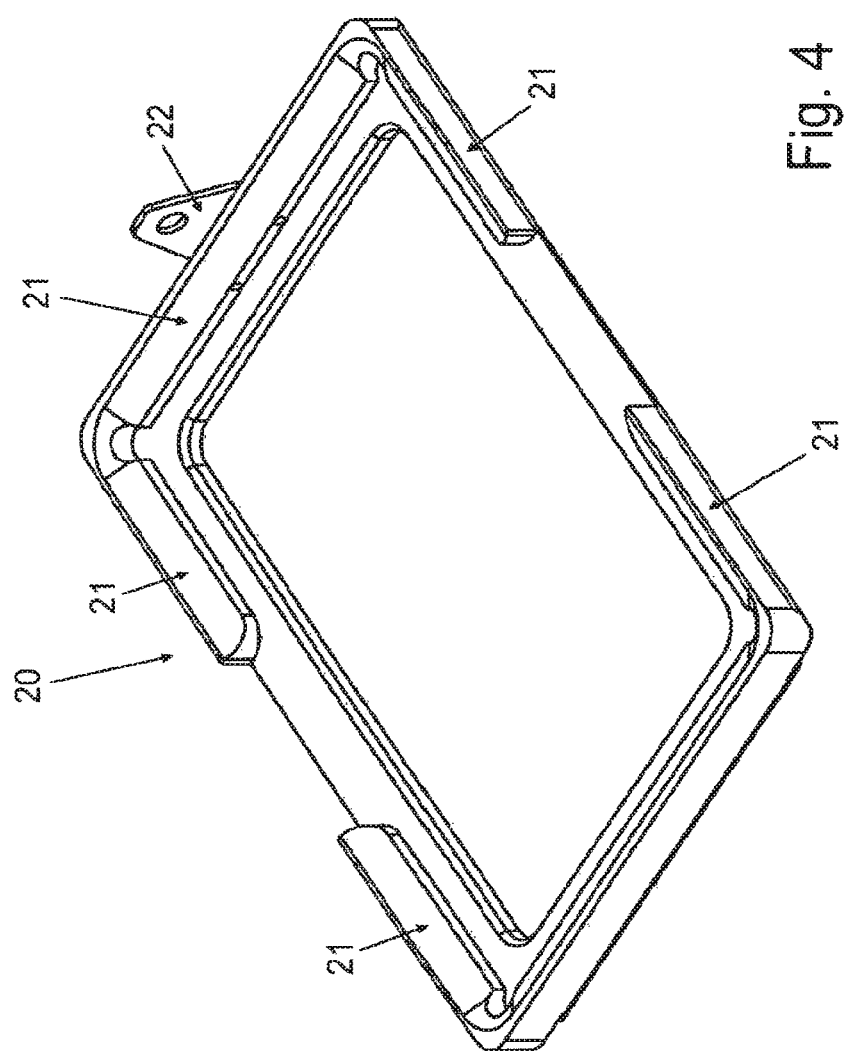
Figure 5:
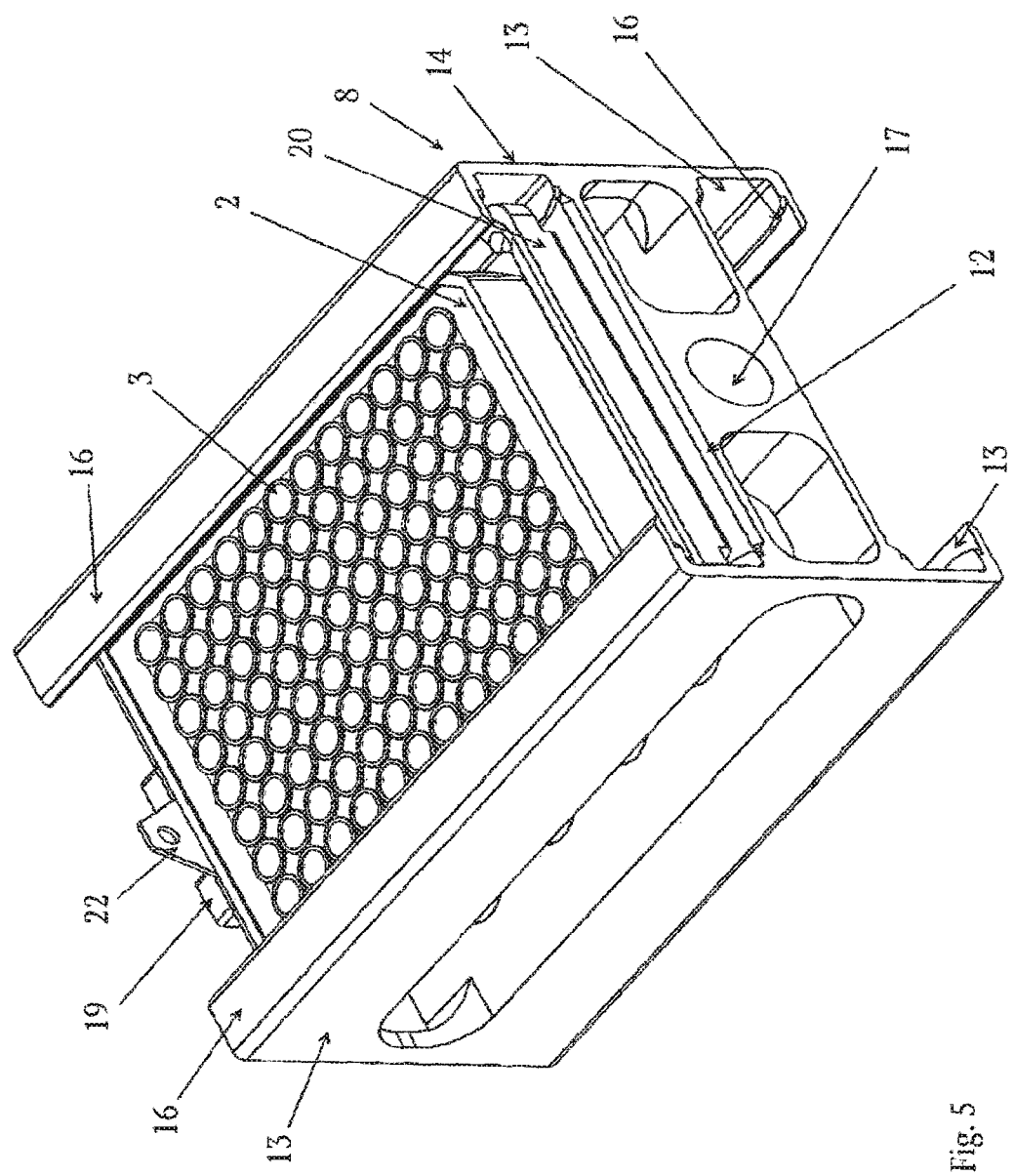
Figure 6:
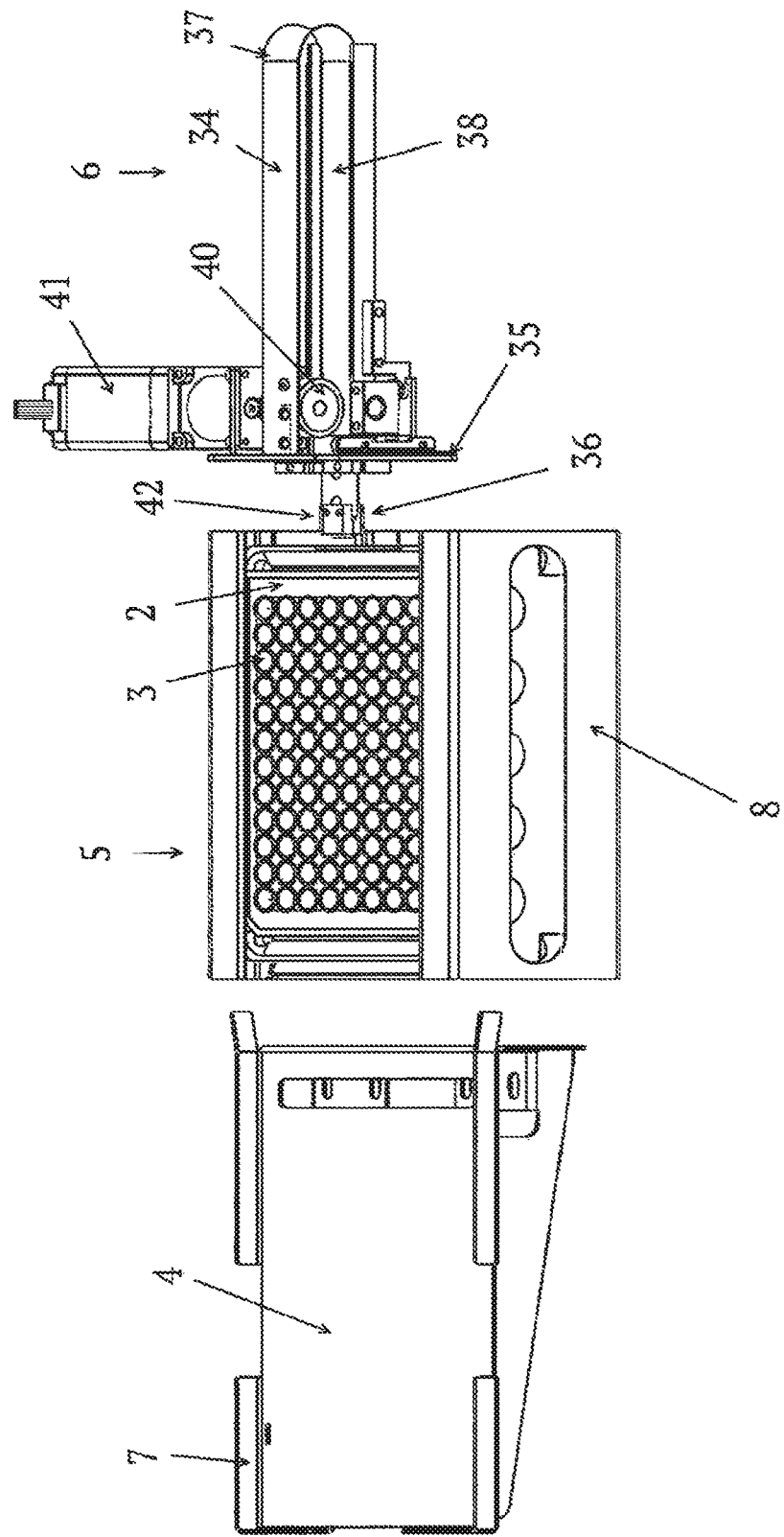
Figure 7:
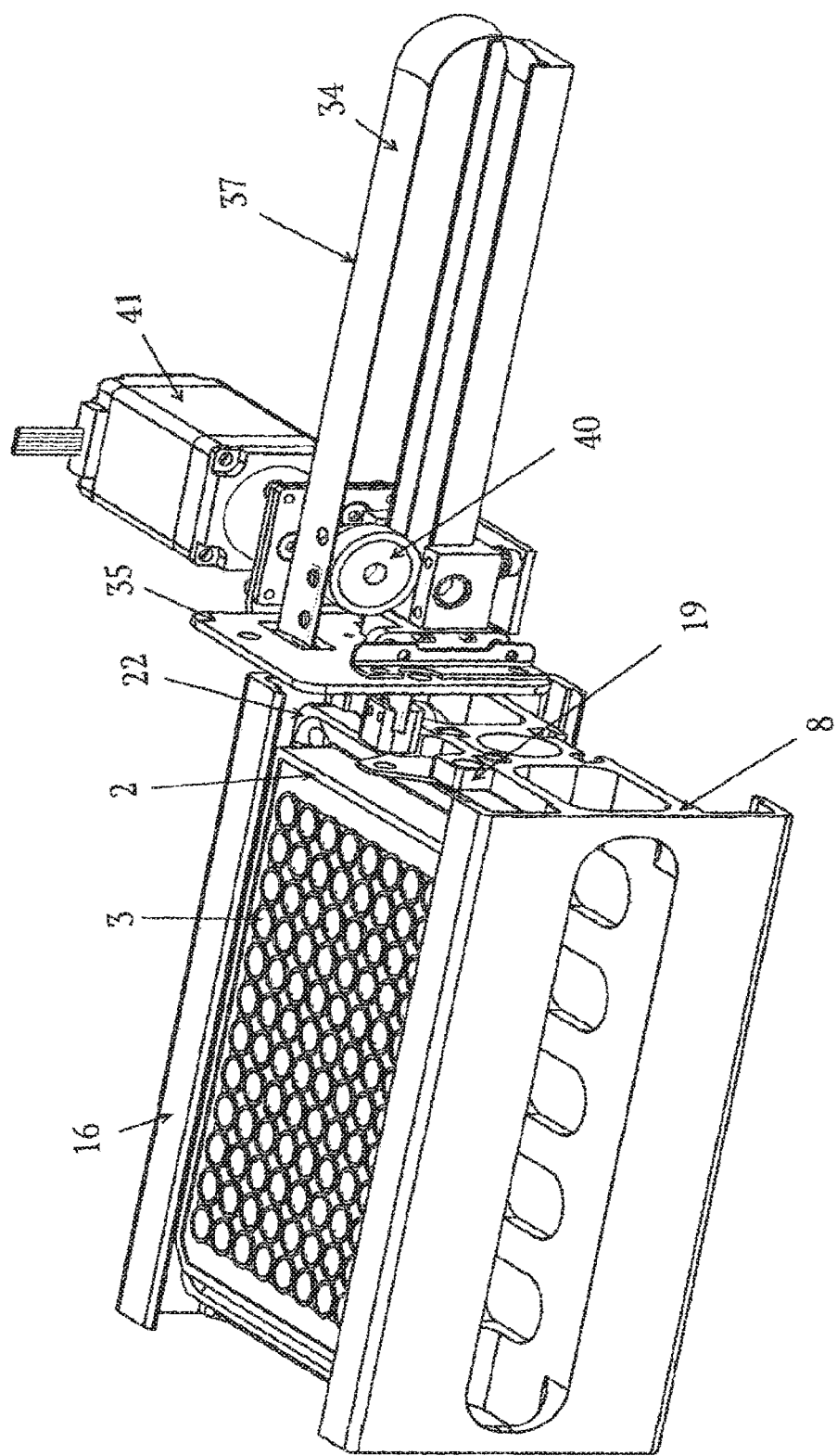

The present invention will be explained in greater detail below by means of examples shown in the accompanying drawings. In the drawings:

FIG. 1 is a perspective view of a first example of a centrifuge according to the invention, FIG. 2 is a perspective view of a rotor and a housing without front side wall of the centrifuge according to FIG. 1, FIG. 3 is a front view of the rotor and the housing without front side wall, FIG. 4 is a perspective view of a reaction vessel unit carrier, FIG. 5 is a perspective view of the rotor containing a reaction vessel unit carrier and a reaction vessel unit, FIG. 6 is a perspective view showing schematically a front platform, the rotor and a loading mechanism, FIG. 7 is a perspective view of the arrangement according to FIG. 6 in the interface section between the rotor and the loading mechanism.

Figure 8:
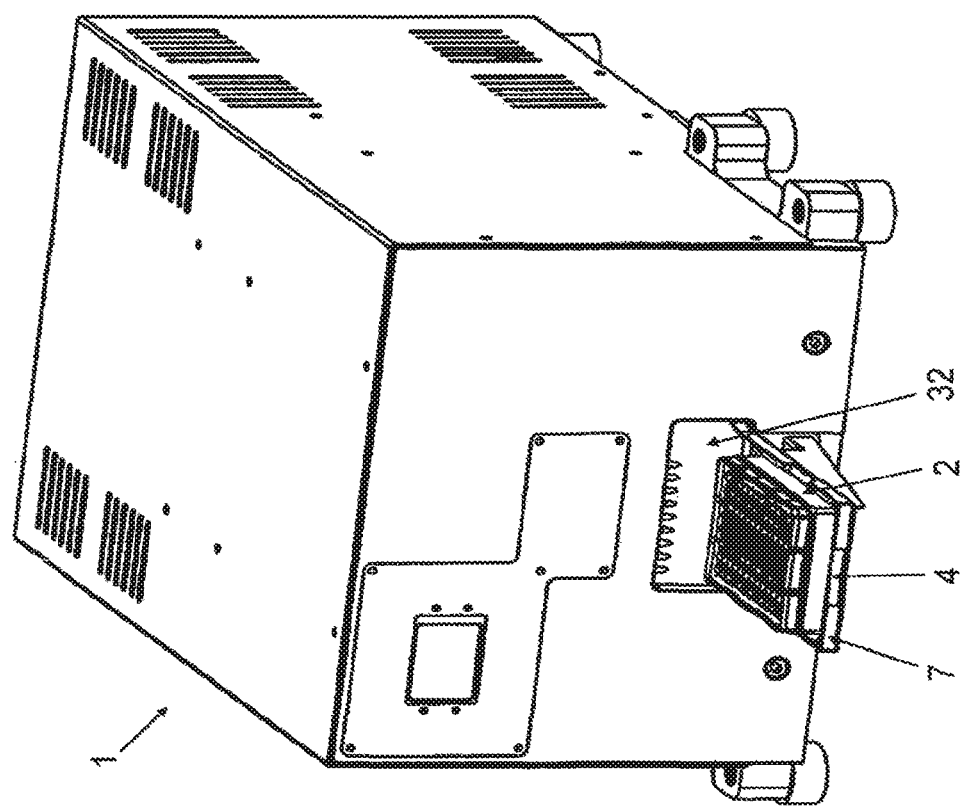
Figure 9:
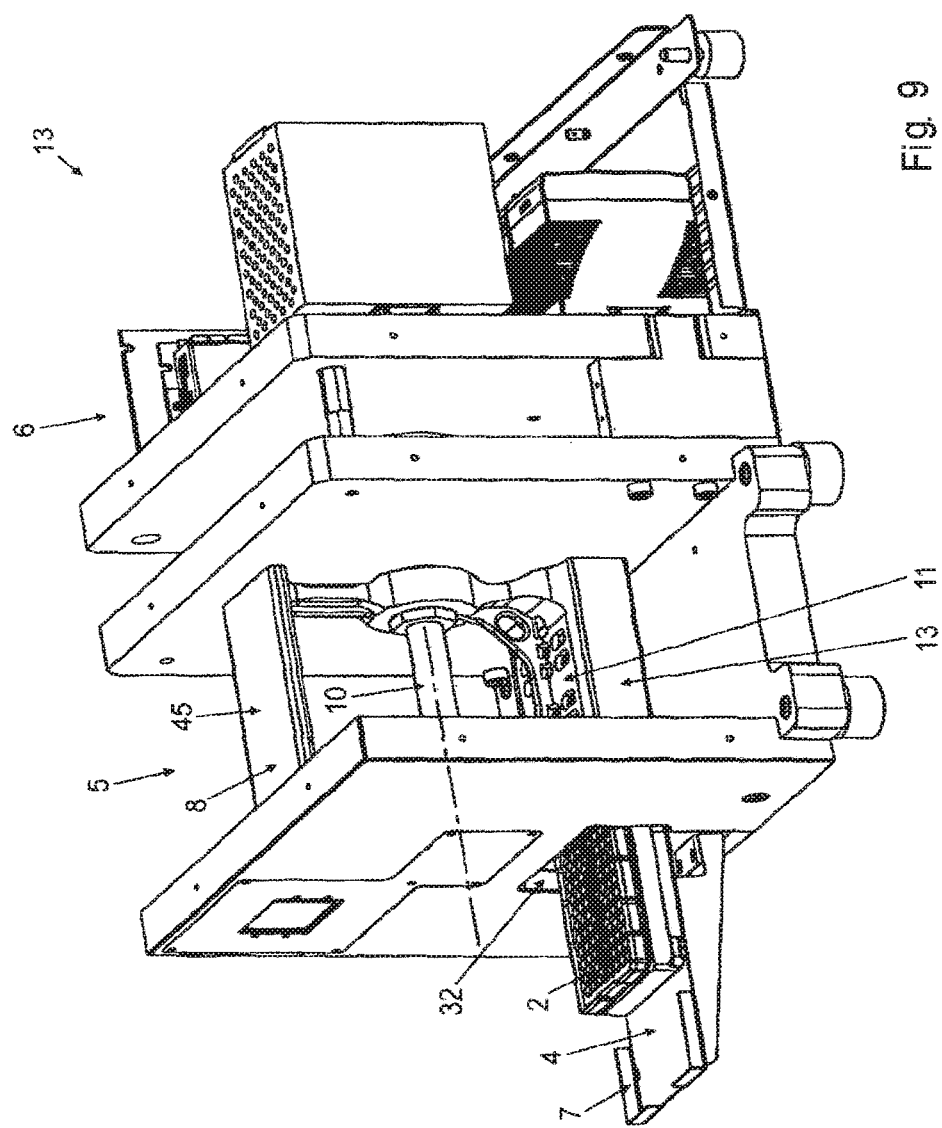
Figure 10:
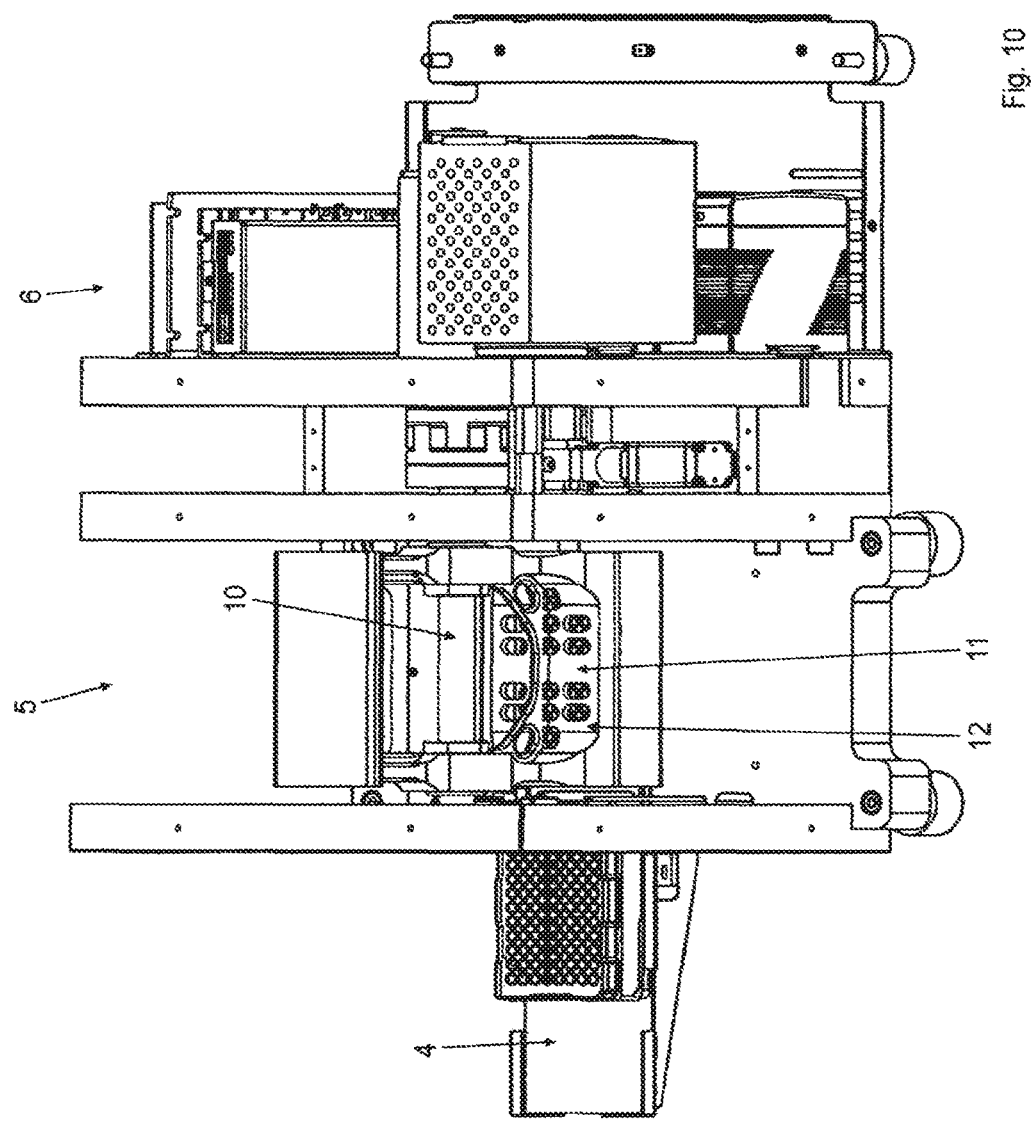
Figure 11:
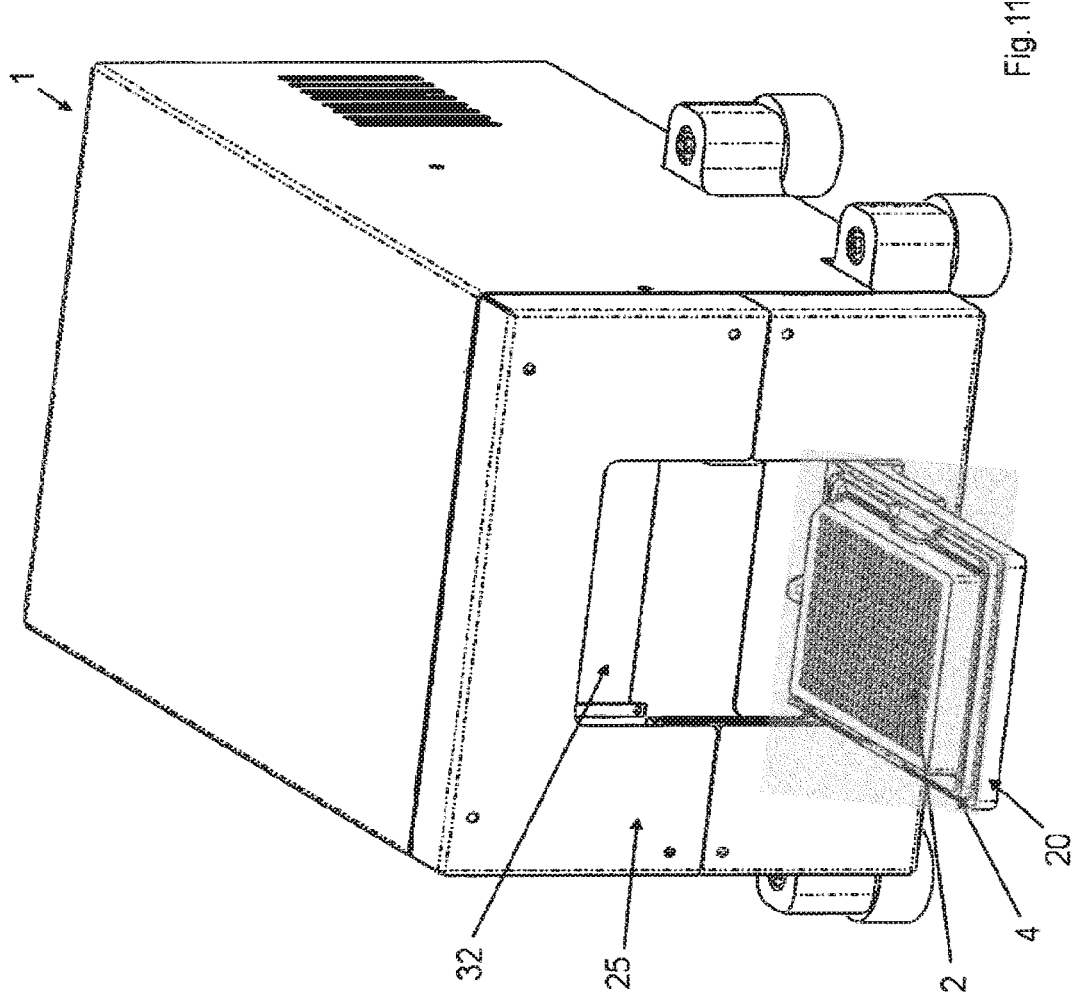
Figure 12:
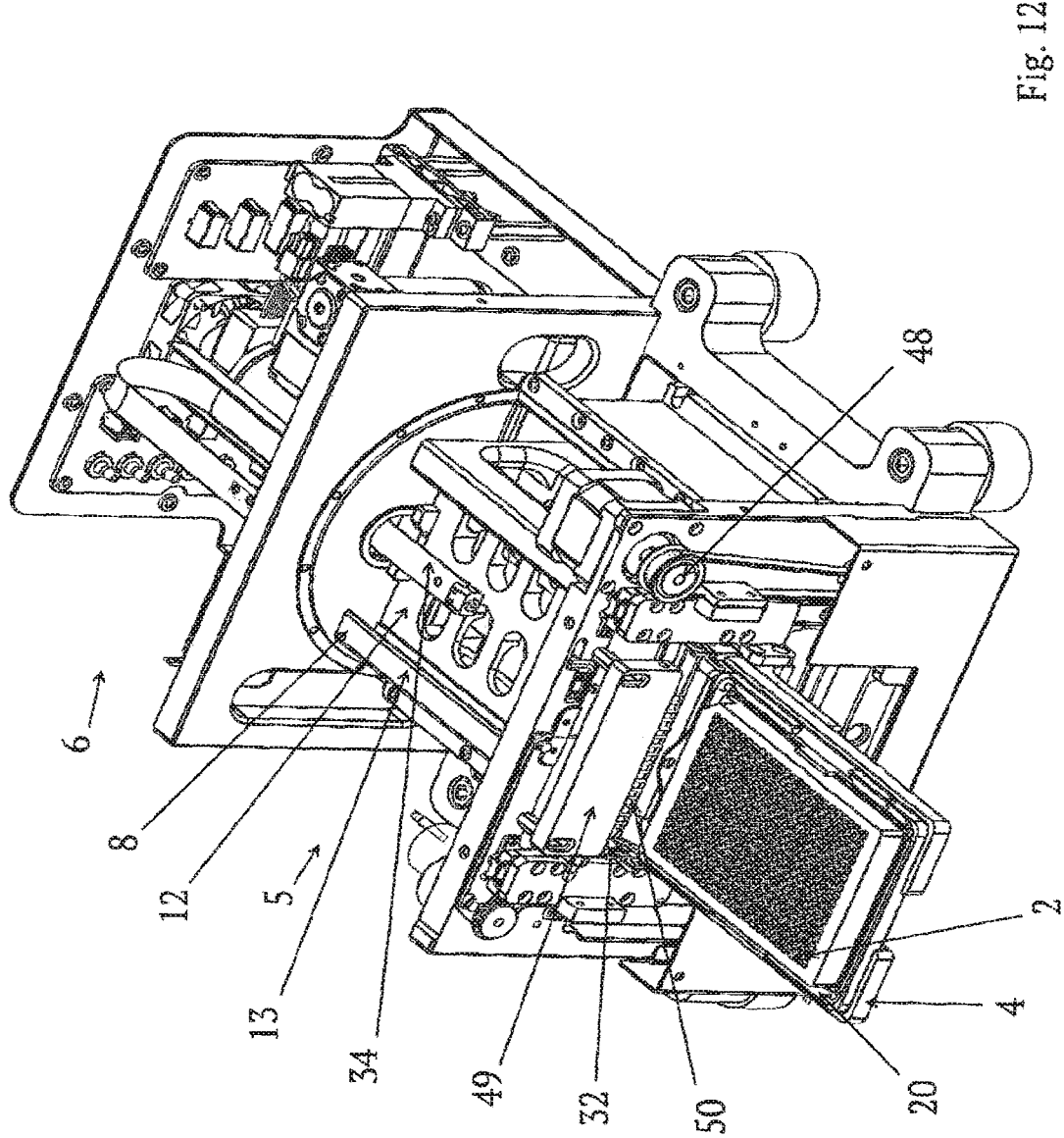
Figure 13:
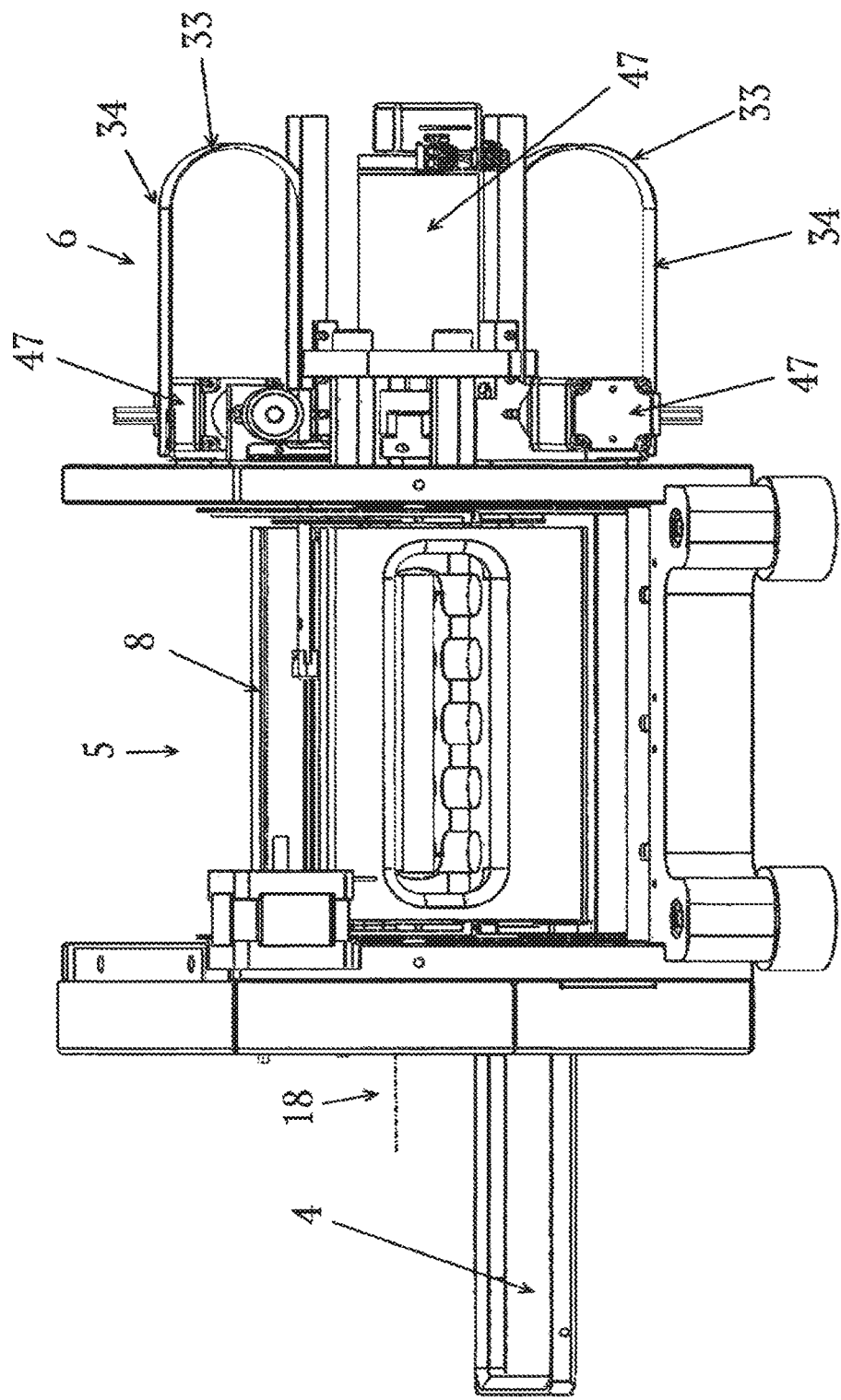
Figure 14:
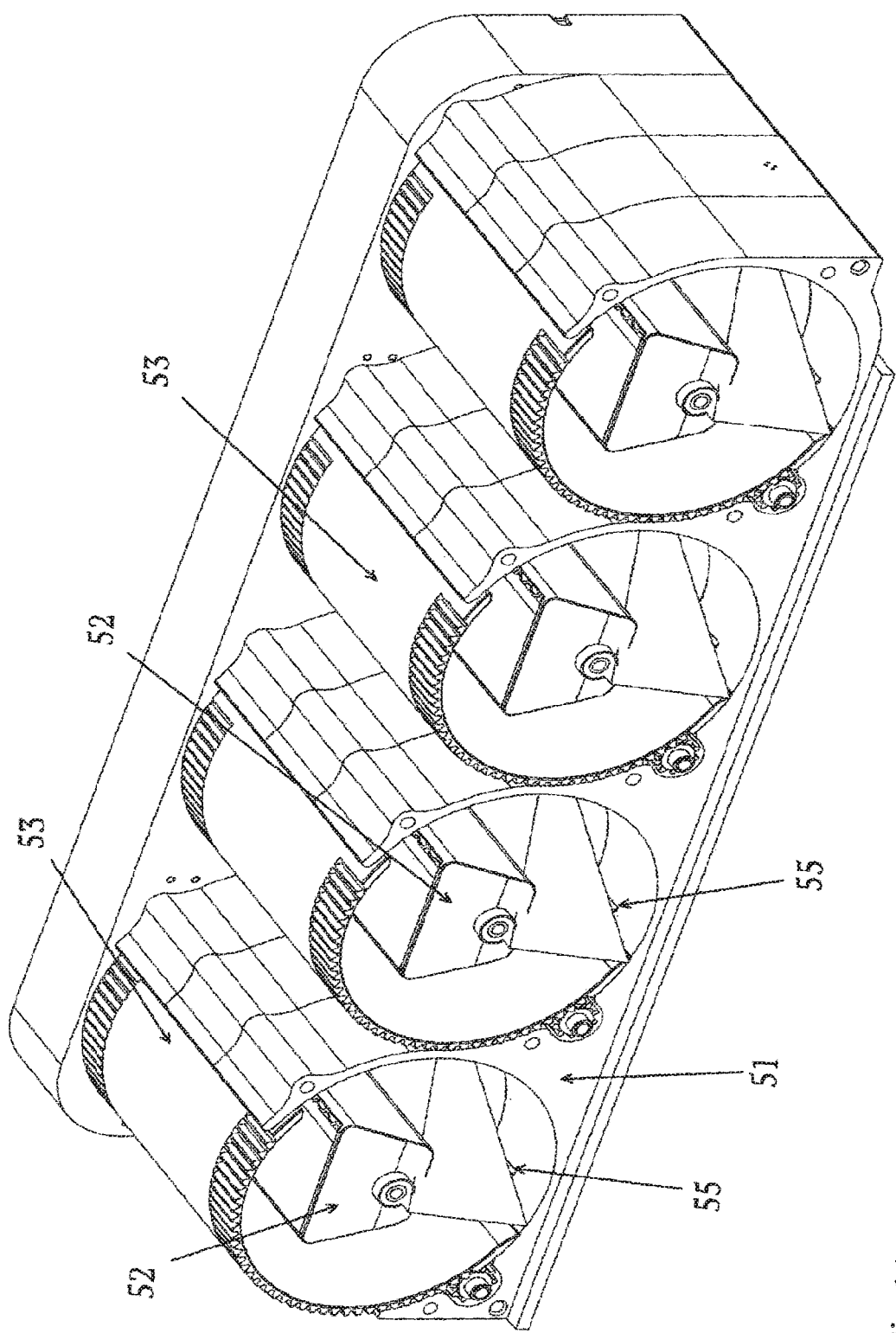
Figure 15:
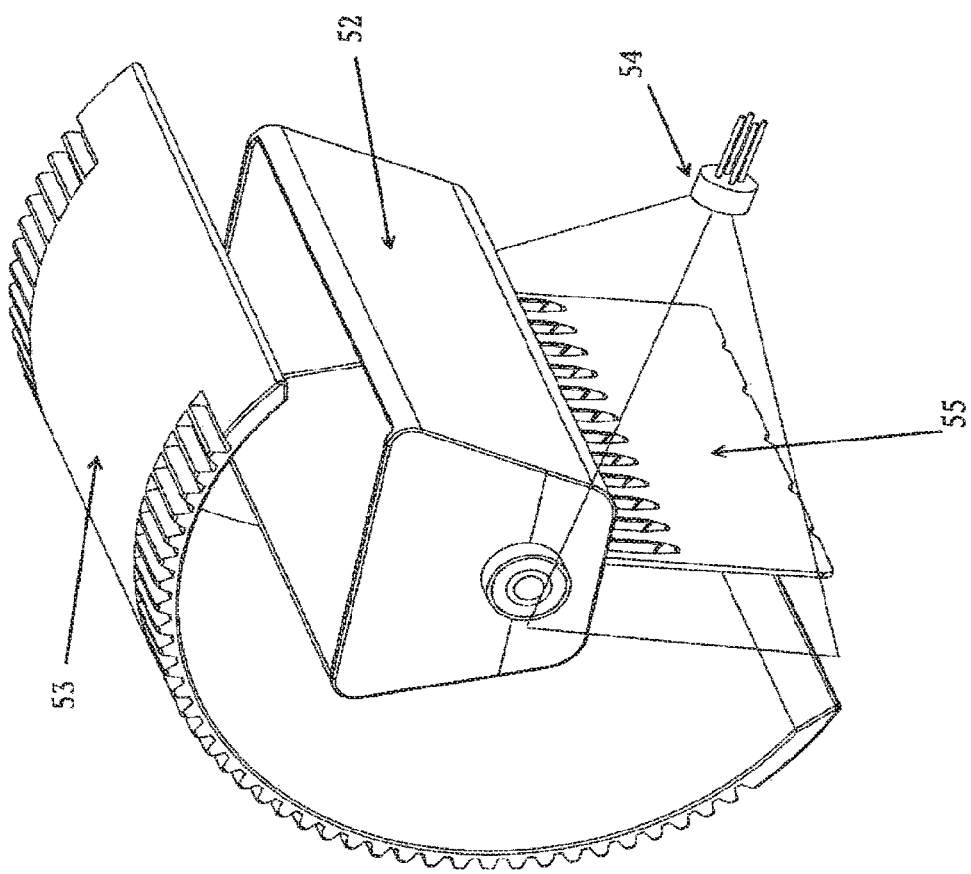
Figure 16:
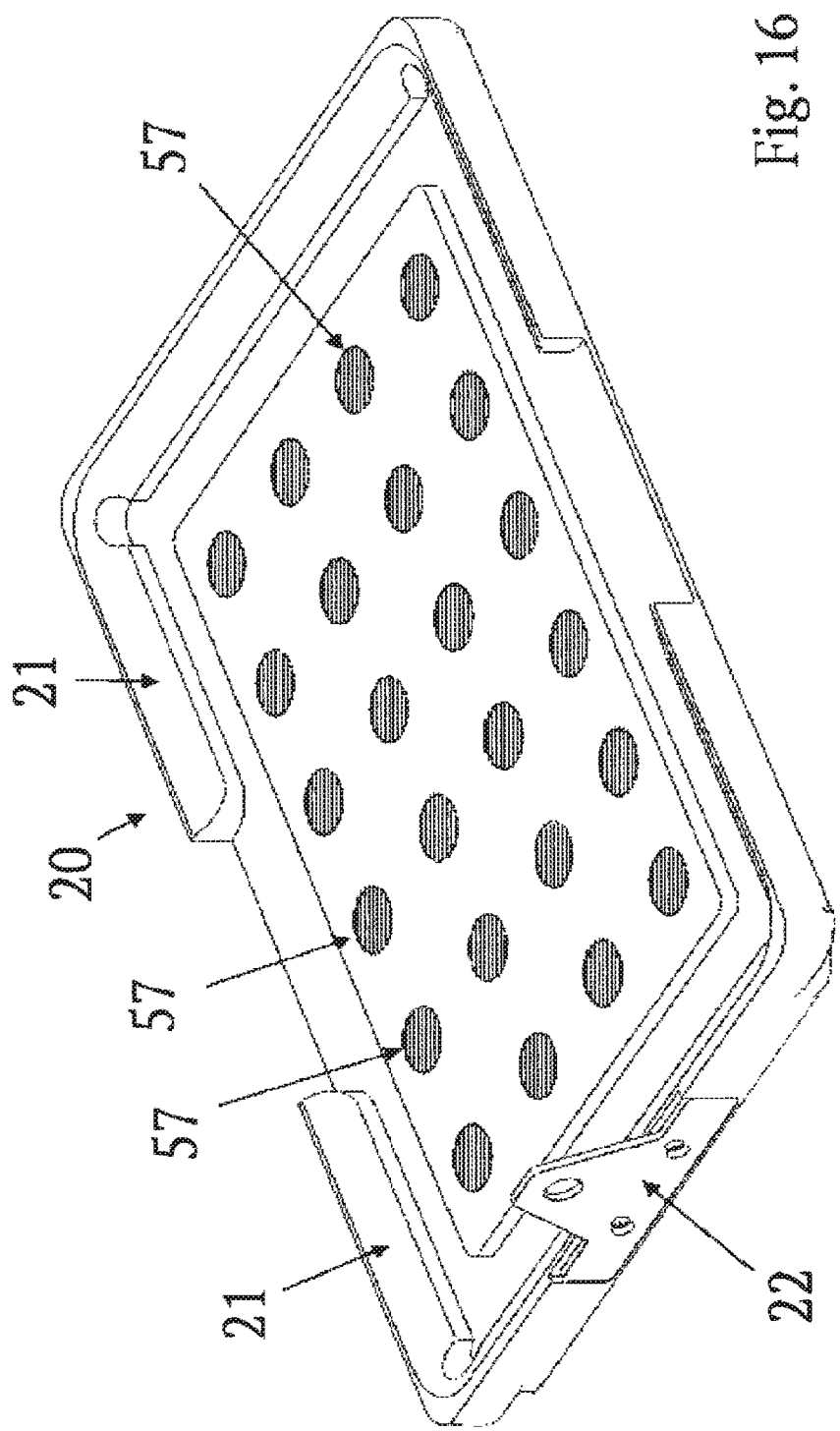

FIG. 8 is a perspective view of a second example of a centrifuge according to the invention, FIG. 9 is a perspective view of the centrifuge according to FIG. 8 without a housing, FIG. 10 is a side view of the centrifuge according to FIG. 8 without a housing, FIG. 11 is a perspective view of a third example of a centrifuge according to the invention, FIG. 12 is a perspective view of the centrifuge according to FIG. 11 without a housing, FIG. 13 is a side view of the centrifuge according to FIG. 11 without a housing, FIG. 14 is a perspective view of a further example of a centrifuge for centrifuging gel cards, wherein the housing is partially cut out, FIG. 15 shows one rotor and an automatic lid of the example according to FIG. 14, and FIG. 16 is a perspective view of a reaction vessel unit carrier.

Figure 17:
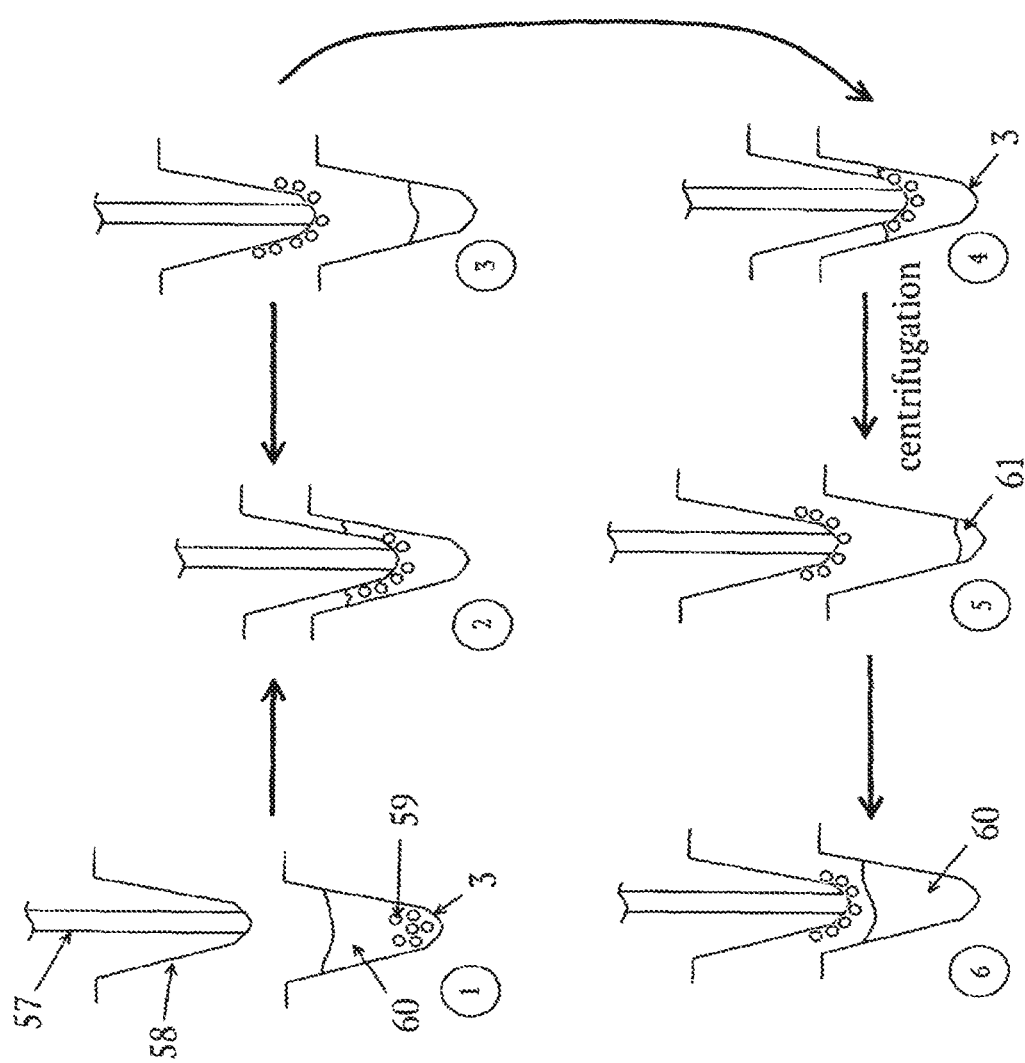

FIG. 17 shows an example for a possible experimental setup for an assay with magnetic beads and magnetic rods for one reaction vessel FIG. 18a-d shows different views of rods and pipetting tips for handling the rods as well as a microplate A first example of a centrifuge (FIG. 1-FIG. 7) is designed for cleaning and washing reaction vessel units. The reaction vessel units are microtiter plates 2. The microtiter plates 2 comprise a plurality of reaction vessels 3 which are arranged in a two-dimensional array. Such microtiter plates typically comprise 96, 384 or 1,536 reaction vessels 3.

The centrifuge 1 comprises a front platform 4, a centrifuge section 5 and a driving section 6 (FIG. 1).

The front platform 4 has, in the top view, a rectangular form which is slightly larger than a standard microtiter plate. Rims 7 are provided on all side edges of the front platform 4 except the one adjacent to the centrifuge section 5.

The centrifuge section 5 comprises a rotor 8 and a housing 9. The rotor 8 is mounted on a horizontal shaft 10 (FIG. 2, 3). The rotor 8 comprises two receptacle sections each for receiving one microtiter plate 2. The receptacle sections are embodied as plate tray 11. The plate trays 11 are each defined by a rectangular base wall 12 and two U-rails 13. Each U-rail 13 comprises a base shank 14 and a side shank 15 mounted on the base wall 12 and a further side shank 16 being distant from the base wall 12. The base shanks 14 are arranged orthogonally to the base wall 12 and the side shanks 15, 16 extend each from the base shank 14 in the direction to the center of the rotor 8, so that the U-rails 13 are arranged opposite with their open sides.

The two base walls 12 of the two plate trays 11 are parallel to each other, wherein central bores 17, through which the shaft 10 is extending, are provided in the section between the two base walls 12. The central bores 17 are arranged in the center of mass of the rotor 8. The center of the shaft 10 defines the rotation axis 18. The rotor 8 is embodied symmetrically with respect to the rotation axis 18.

In the present embodiment the base walls 12, the U-rails 13 and the sections in between the base walls 12 are made from one single piece of aluminum.

On the front side of the rotor 8 the plate trays 11 are open so that a microtiter plate can slide into the plate tray 11. At the rear side of the rotor 8 a stopper 19 is provided. The stopper 19 comprises preferably a magnetic element.

The section in between the base walls 12 is cut out as far as possible and bores are provided in the base walls 12 to minimize the moment of inertia.

In the present embodiment plate trays 11 are designed for receiving a microtiter plate 2 together with a microtiter plate carrier 20 (FIG. 4). The microtiter plate carrier 20 is a rectangular frame having rims 21 at the side edges, wherein the inner surfaces of the rims 21 define with a small play the position of a microtiter plate 2 on the microtiter plate carrier 20. The upper surfaces of the rims are tilted inwardly so that a microtiter plate is sliding into the section which is defined by the rims 21.

The microtiter plate carrier 20 comprises at one side edge a coupling element made of magnetic material, particularly of a ferromagnetic material. This coupling element 22 can cooper-ate with the magnetic stopper 19 and the rotor 8.

The distance of the distant or outer side shank 16 to the inner side shank 15 or the base wall 12 is so designed that a microtiter plate 2 and a microtiter plate carrier 20 are held in radial direction with small play. This play is so that the microtiter plate carrier 20 and a microtiter plate 2 can be easily slid into and out of the plate tray 11. The outer side shanks 16 are so small that they do not cover any reaction vessel 3 of a microtiter plate 2.

The rotor 8 is surrounded by a housing 23. The housing 23 comprises a cylindrical jacket wall 24, a front side wall 25 and a rear side wall 26 (FIG. 1, 2). The jacket wall 24 comprises a lower and upper half shell 27, 28, which are connected by outwardly arranged flanges 29. The inner surface of the jacket wall 24 is substantially in the form of a cylinder and arranged coaxially to the rotation axis 18. The interior space of the housing 23 defined by the jacket wall 24, the front side wall 25 and the rear side wall 26 is called in the following as "rotor space" 56.

A drain 30 is provided in the lower section of the inner surface of the jacket wall 24. The drain is embodied in the form of a groove, wherein the depth of the groove is continuously increasing in the direction to the rear side of the housing 23 (FIG. 2). At the rear side of the housing 23 an aspiration pump (not shown in the drawings) is connected to the drain 30 for discharging fluid from the housing 23. The drain 30 forms with the inner surface of the jacket wall 24 sharp edges.

A gap g between the radial outmost portions of the rotor 8 and the inner surface of the jacket wall 24 is preferably not larger than one millimeter, particularly not larger than 0.75 millimeter and most preferably not larger than 0.5 millimeter. The smaller the gap is the stronger a circular airstream is generated when the rotor 8 is rotating in the housing 23. However, this gap g should preferably not be smaller than 0.1 millimeter and in particular not smaller than 0.2 millimeter or 0.3 millimeter, because such small gaps could cause the rotor to come into con-tact with a fluid film on the inner surface of the jacket wall 24. This is explained in further detail below.

The flanges 29 of the lower half shell 27 are connected to supports 31 for fixing the housing 23 onto a platform (not shown).

The front side wall 25 comprises an opening 32 in the form of a rectangular slid. An automatic door is provided for closing the opening 32. The opening 32 is arranged in the level of the front platform 4. In the loading position, the rotor 8 is arranged horizontally with its base walls 12, wherein the base wall of the upper plate tray 11 is arranged on the same level as the front platform 4, so that a microtiter plate carrier 20 and a microtiter plate 2 can slide horizontally from the front platform 4 into the upper plate tray 11 and vice versa.

The driving section 6 comprises a motor (not shown) for rotating the shaft 10 and the rotor 8. The motor is connected to a control unit for controlling the rotation speed.

The driving section 6 also comprises a loading mechanism 33 for loading and unloading the centrifuge 1 with a reaction vessel unit, which, in the present embodiment, is a microtiter plate 2.

The loading mechanism 33 comprises a flexible elongated beam 34 for extension and retraction of a microtiter plate 2 or a microtiter plate carrier 20 together with a microtiter plate 2. The flexible elongated beam 34 is made of a stripe of metal sheet which is slightly bent transverse to its longitudinal extension. Thus, the metal sheet provides certain stiffness if it is extended linearly and on the other hand it can be bent around an axis transverse to the longitudinal extension. Such bent metal sheet stripes are well known from metal measuring tapes.

In the present embodiment one end of the beam 34 is fixed on an inner wall 34 of the driving section 6, wherein the beam is extending from the inner wall 35 rearwards. The beam 34 is bent by a U-turn so that a free end 36 of the beam is directed forwardly and the beam is extending through a slid in the inner wall 35. Thus, the beam comprises an upper strand 37 fixed to the inner wall 35 and a lower strand 38 extending through the slid of the inner wall 35. The strand 38, which is extending through the inner wall 35 and which comprises the free end 36, is clamped between two wheels 40, wherein one of the two wheels 40 is driven by a stepper motor 41. Only one of the two wheels is shown in the drawings. The free end 36 of the beam 34 is provided with a magnetic element 42. The beam 34 can be actuated by means of the stepper motor 41 so that the free end 36 with its magnetic element 42 is ex-tended or driven through the centrifuge section 5 and through the opening 32 in the front side wall 25. Thus, the free end 36 of the beam 34 reaches in the maximum extended position the area of the front platform 4. In the maximum retracted position the free end 36 of the beam 34 is arranged behind the rotor 8 and particularly out of the centrifuge section 5, so that the rotor 8 can be freely rotated.

The loading mechanism 33 can be coupled to a microtiter plate carrier 20, which is placed on the front platform 4, just by extending the beam 34 until the magnetic element 42 of the beam couples through the coupling element 22 of the microtiter plate carrier 20. By retracting the beam 34 the microtiter plate carrier 20 is drawn into one of the plate trays 11 of the rotor 8. When the microtiter plate carrier 20 abuts to the stopper 19, the coupling between the magnetic element 42 of the beam 34 and the coupling element 22 of the microtiter plate carrier 20 is released by further retracting the beam and simultaneously the coupling element 22 of the microtiter plate carrier 20 is coupled to the magnetic element of the stopper 19 and thus fixed in position in the rotor 8.

This loading mechanism 33 allows coupling the centrifuge 1 to any transport system for transporting microtiter plates in an automatic labor robot. The labor robot just has to put a microtiter plate 2 onto a microtiter plate carrier 20 located at the front platform 4. Then the loading mechanism 33 can load and unload the rotor 8. It is also possible to place the centrifuge 1 without a front plate directly adjacent to a transport belt for transporting microtiter plates, wherein microtiter plates 2 can be withdrawn from the transport belt with the loading mechanism 33 and can be put onto the transport belt again. In the present embodiment a microtiter plate carrier 20 having a coupling element 22 is used. It is also possible to provide the microtiter plates 2 with such coupling elements 22 so that there is no need for a microtiter plate carrier.

A further advantage is that the loading mechanism 33 is placed on the rear side of the centrifuge section 5 so that the centrifuge 1 can be coupled to an existing laboratory robot without any intermediate devices. This facilitates the integration of the centrifuge into the existing laboratory robots.

Furthermore, the loading mechanism 33 needs only a small installation space. This installation space can even further be reduced if the beam is winded up on a reel instead of bending it into two strands.

The centrifuge 1 is used for cleaning microtiter plates 2. A microtiter plate 2 containing liquid in the reaction vessels 3 is put on a microtiter plate carrier 20 which is located on the front platform 4. The microtiter plate carrier 20 is drawn together with the microtiter plate 2 into one of the plate trays 11 by means of the loading mechanism 33. The microtiter plate carrier 20 is magnetically coupled to the stopper 19.

The rotor is rotated, wherein the rotation speed is controlled by a control unit in a range of 5-3,000 RPM. Due to the centrifugal force, the liquid is expelled from the reaction vessels 3. By this centrifugal washing it is possible to reliably remove liquid even from small reaction vessels, in which capillary forces occur. Therefore, liquid can be reliably removed from microtiter plates having 384 or 1,536 reaction vessels.

During the centrifugation the liquid is expelled from the reaction vessels 3 and drops of the liquid are impinged on the inner surface of the jacket wall 24. The drops form a liquid film on the inner surface of the jacket wall 24. Due to the rotation of the rotor 8 and the small gap between the rotor 8 and the inner surface of the jacket wall 24, a strong rotational airstream is caused, which forces the liquid film on the inner surface of the jacket wall 24 to flow in the rotational direction of the rotor. Thus, the liquid is driven to the drain 30, from which the liquid is withdrawn by means of the aspiration pump.

For reliably withdrawing the liquid from the internal space of the housing 23, the rotation speed is preferably at least 500 RPM, particularly at least 1,000 RPM and most preferably at least 1,500 RPM. The rotation speed should be adjusted in dependence on the surface tension of the liquid and the gap between the rotor 8 and the jacket wall 24.

Preferably the rotational direction is reversed at the end of the centrifuging step so that a 40 liquid film on the inner surface of the jacket wall 24 on the rear side of the drain 30 with respect to the first rotational direction is driven into the drain 30 by rotating the rotor 8 with a second rotational direction.

It has been shown that the residual volume of the liquid, which remained in a reaction vessel after centrifuging a microtiter plate, was smaller than 0.01 µl applying an amount of liquid of e.g. 200 µl. The liquid can be a washing solution, so that with one washing step a dilution ratio of 20,000:1 is achieved. Ordinary washing machines for washing microtiter plates provide a dilution ratio of 40:1. Using such a centrifuge increases the dilution ratio 5,000 times.

Microtiter plates with coated reaction vessels are used for immunoassay processes. With the coating, a first specific binding member is immobilized in the reaction vessel. In typical immunoassay processes, such as ELISA, a second specific binding member forms a complex with the first specific immobilized binding member. Non-specifically bound components have to be removed from the reaction vessels. With the centrifuge 1 this can be achieved in a low number of washing steps by dispensing a certain washing solution into the reaction vessel 3, centrifuging the microtiter plate and eventually repeating the washing step.

If microtiter plates with large reaction vessels are used, such as standard microtiter plates having 96 reaction vessels, it can be advantageous if at the beginning the rotor is only rotated once by 180°, so that the openings of the reaction vessels 3 are directed downwards. A large amount of the liquid is then flowing out of the reaction vessels. This can be supported by a shaking movement of the microtiter plate, wherein the rotor is moved forth and back by a small angular distance of e.g. 5° to 20°.

It is also known to immobilize a first specific binding member on magnetic beads. The magnetic beads can be put into reaction vessels of a microtiter plate, wherein the immunoassay (Enzyme Immuno assay, EIA; Chemiluminescent Immuno Assay, CLIA) processes can be carried out. In any case, these magnetic beads have to be washed.

The difference in the efficiency of washing of beads or other solid surfaces is dependent on the number of washing steps needed. A typical high sensitivity assay (e.g. by the technology of the company Quanterix, USA) requires up to 12 subsequent washing steps because the residual volume has to be diluted by a factor of more than $10^{18}$ (!!). Washing by centrifugation leads to a substantial improvement of assay workflow by cutting the number of washing steps drastically.

For washing magnetic beads a microtiter plate carrier 20 (FIG. 16) is provided comprising a plate having a number of magnetic elements 57. The number can be one for one big magnet covering the plate area or more than one, wherein the magnetic elements are regularly distributed on said plate. These magnetic elements 57 apply a magnetic field to the reaction vessels. During the washing step, the rotational speed of the centrifuge is to be adjusted that the centrifugal force exerted onto the magnetic beads is smaller than the magnetic force between the magnetic beads and the magnetic elements of the microtiter plate carrier. Both the magnetic force and the centrifugal force depend on the size and material of the magnetic beads. It has been shown that it is reliably possible to wash magnetic beads without losing any magnetic bead. In a calibration step, magnetic beads contained in the liquid that is with-drawn by the aspiration pump from the rotor space 56 are detected, wherein the rotation speed is gradually increased. This can be done by means of a magnetic sensor, such as a hall sensor located adjacent to the outlet of the drain 30. After detecting a magnetic bead in the liquid, the actual rotation speed is captured and reduced by a certain, small predetermined amount. This rotation speed is used in the subsequent washing steps for washing magnetic beads.

The above explained first example of a centrifuge 1 comprises preferably a cylindrical jacket wall 24, which is made of a thermal conducting material, such as aluminum. The jacket wall can be provided with the cooling means, so that the inner surface of the jacket wall 24 can be cooled. The inner surface of the jacket wall 24 is preferably kept cooler than the rotor 8 and any other part inside the jacket wall 24. Thereby it is secured that fluid condenses only on the inner surface of the jacket wall 24 and not on the rotor 8 or any other part. The fluid condensed on the inner surface of the jacket wall 24 is securely discharged via the drain 30 from the housing 23, as described above. Preferably, the inner surface of the jacket wall 24 is kept cooler than at least 2° C. or 3° C. or even cooler than 5° C. than the other parts inside the rotor space 56 and/or cooler than the gas contained in the rotor space 56, so that fluid originating from the liquid in the reaction vessels, which is vaporized into the gas contained in the rotor space is re-condensed only on the inner surface of the jacket wall 24. By cooling the jacket wall 24, it can be secured that volatile liquids are withdrawn from the gas atmosphere in the housing 23 and completely discharged from the housing 23.

The cooling means for cooling the jacket wall 24 is preferably a Peltier element, particularly a Peltier foil, which covers the outer surface of the jacket wall 24. Such a Peltier element conveys the heat of the jacket wall 24 radially outward. Thus, the inner surface of the jacket wall 24 is kept cool and the outer side of the Peltier element is warm. Therefore, condensing of fluid appears only on the inner surface of the jacket wall 24 and not in any other part of the centrifuge.

The centrifuge 1 can comprise a venting system for exchanging the gas or air, respectively in the rotor space 56. The venting system comprises a blower coupled to an opening e.g. in the rear side wall 26. When the opening 32 in the front side wall 25 is opened, the air in the rotor space 56 can be exchanged by activating the blower. The exchange of the gas or air is usually carried out between two consecutive centrifuging processes.

The venting system can also be combined with a heating/cooling device so that the air introduced into the rotor space 56 is heated or cooled. Such a venting system forms a tempering device for tempering the interior of the rotor space 56 to a predetermined temperature.

A second example of a centrifuge (FIG. 8-FIG. 10) is designed for centrifuging reaction vessel units. The reaction vessel units are microtiter plates 2. The second example of the centrifuge 1 is similarly embodied as the first example so that similar parts are designated with the same reference signs. These parts are identical to the ones of the first example, as far as there is no different explanation.

This centrifuge 1 comprises a front platform 4, a centrifuge section 5 and a driving section 6 (FIG. 9). The centrifuge section 5 comprises a rotor 8 which is mounted on a horizontal shaft 10 (FIG. 9). The rotor comprises one receptacle section or plate tray 11 for receiving one microtiter plate 2. The plate tray 11 is defined by a rectangular base wall 12 and two U-rails 13.

The base wall 12 is connected by means of legs 43 with a flange 44 defining a central bore 17 through which the shaft 10 is extending. In the second example, the distance between the base wall 12 and the shaft 10 is much larger than in the first example. With such a rotor reaction vessel units can be centrifuged having a lateral extension with nearly the same centrifugal effect in all reaction vessels. The distance of the plate tray 11 to the rotation axis 18 is preferably larger than the lateral extension of the reaction vessel unit, particularly at least 1.5 times or 2 times larger than the lateral extension of the reaction vessel unit.

Diametrically opposite to the receptacle section or plate tray 11, a counterweight 45 is fixed to the flanges 44 by means of further legs 46. A further plate tray could be provided instead of a counterweight 45, which is embodied for receiving a microtiter plate or a microtiter plate carrier together with a microtiter plate to form an adjustable counterweight to the kind of microtiter plate used in the other plate tray 11.

The opening 32 in the front side wall 25 is embodied at the level of the lowest position of the plate tray 11, which is the loading position of the rotor 8. The front platform 4 is provided on the same level as the base wall 12 of the plate tray 11 in the loading position, so that a microtiter plate or a microtiter plate on a microtiter plate carrier can slide from the front platform 4 onto the base wall 12 and vice versa, wherein the openings of the reaction vessels 3 of the microtiter plate 2 are directed to the shaft 10.

The opening 32 in the front side wall 25 can be closed by an automatic door (not shown).

The centrifuge 1 comprises a motor 47 for driving the shaft 10 and the same loading mechanism 33 as in the first example, wherein the flexible elongated beam 34 is arranged with its free end 36 and magnetic element 42 slightly above the level of the base plate 12 in the loading position of the rotor 8 for loading and unloading a microtiter plate or a microtiter plate on a microtiter plate carrier.

This centrifuge is designed for centrifuging a microtiter plate 2. As the distance between the microtiter plate and the shaft 10 or rotation axis 18 is large, nearly the same centrifugal acceleration is exerted to the fluid in the different reaction vessels 3. Therefore, the same centrifugation effect is achieved independently of whether the fluid is located in a center reaction vessel or a lateral reaction vessel.

A control unit is provided to control the speed as well as the acceleration of the rotor. The speed of the rotor is in the range of 100 RPM to 3,000 RPM. The acceleration and deceleration of the rotor lies in the range of 100-1,200 RPM/s. When starting the rotor, it shall be accelerated, so that, after a turn of about 180°, at least a centrifugal acceleration of 1 g should be applied, so that no fluid drops out of the reaction vessels with its openings directing downwardly. Microtiter plates having deep well reaction vessels can be accelerated as fast as possible. However, accelerating microtiter plates with small wells as reaction vessels could cause a contamination by sloshing of fluid from one reaction vessel to a neighboring reaction vessel due to the acceleration. The danger of such a sloshing contamination depends on the filling amount of the reaction vessels as well as on the form of the reaction vessels. It has been shown that with an acceleration up to 500 RPM/s to 1,200 RPM/s, no contamination due to sloshing occurs.

A third example of a centrifuge 1 (FIG. 11-FIG. 12) is designed for cleaning and washing reaction vessel units as well as for centrifuging reaction vessel units. This centrifuge 1 is embodied similarly as the one of the first example. Similar parts of the centrifuge are designated with the same reference signs as in the first example.

The centrifuge 1 comprises a front platform 4, a centrifuge section 5 and a driving section 6 (FIG. 12, 13).

The front platform 4 is coupled to a lifting means 48 to move the front platform 4 up and down, wherein the front platform 4 is kept in a horizontal position. The opening 32 in the front side wall 25 is larger than in the first example, so that it covers both the top most and lowest position of the plate tray 11 of the rotor 8. The front platform 4 can be moved by means of the lifting means 48 between the top most and lowest position of the base wall 12 of the plate tray 11.

In the upper position, the front platform 4 is on the same level as the base wall 12 in the uppermost position of the plate tray 11, so that a microtiter plate or a microtiter plate on a microtiter plate carrier can be slid horizontally from the front platform 4 onto the base wall 12 and vice versa. In the upper position of the front platform 4, the rotor is loaded or unloaded with a microtiter plate directed with its opening radially outwardly.

In the lower position, the front platform 4 is on the same level as the base wall 12 of the plate tray 11 in the lowest position, so that a microtiter plate or a microtiter plate on a microtiter plate carrier can slide from the front platform 4 onto the base wall 12 and vice versa. In this position, the plate tray 11 is loaded or unloaded with the microtiter plate, wherein the openings of the microtiter plate are directed radially inwardly or in a direction to the shaft 10.

In the upper position, the rotor can be loaded with a microtiter plate for cleaning or washing reaction vessels, and in the lower position the rotor can be loaded with a microtiter plate for centrifuging the content of the reaction vessels. This centrifuge is therefore called hybrid-centrifuge because it is adapted for both cleaning and washing microtiter vessels on one side and centrifuging the content of microtiter plates on the other side.

The centrifuge 1 comprises two loading mechanisms 33, each having a flexible elongated beam 34 and a step motor 41 for actuating the corresponding flexible elongated beam 34. Furthermore, a motor 47 is provided for actuating the shaft 10 for revolving the rotor 8 around the rotation axis 18.

A dispensing bar 49 (FIG. 12) is provided adjacent to the upper section of the opening 32 of the front side wall 25. This dispensing bar 49 comprises a plurality of dispensing nozzles 50 arranged in line. For each reaction vessel in a column of the microtiter plate, a corresponding dispensing nozzle 50 is provided in the dispensing bar 49. The dispensing bar 49 is connected to a reservoir of dispensing fluid, particularly washing fluid, and a pump, so that the dispensing fluid can automatically be dispensed via the dispensing nozzle 50 into the reaction vessels. The dispensing fluid can be kept heated in the reservoir. The dispensing of a heated washing solution improves the washing efficiency.

With the loading mechanism 33, each column of reaction vessels of a microtiter plate can be individually arranged below the dispensing bar 49 for dispensing fluid into the reaction vessels of the corresponding column. With this dispensing bar integrated into the centrifuge, it is possible to very quickly repeat several washing steps comprising a cleaning or a washing step by centrifugation of the microtiter plate and a dispensing step in between the individual centrifugation steps.

The above described examples show centrifuges which are embodied for cleaning, washing, and/or centrifuging microtiter plates. FIGS. 14 and 15 show a further example of a centrifuge for centrifuging gel cards. Gel cards are reaction vessel units having a plurality of reaction vessels which are arranged linearly side by side. Such gel cards have deep wells.

The centrifuge 1 according to the fourth example comprises a centrifuge housing 51 which accommodates four centrifuge units, each comprising a rotor 52 and an automatic lid 53 for individually opening and closing each centrifuge unit. Each rotor 52 is individually driven by a motor (not shown), wherein the rotors 52 can be independently rotated.

Each centrifuging unit comprises a camera 54 for detecting the gel cards 55, which is set in a corresponding rotor 52. The camera 54 comprises a light source.

For taking a picture, the rotation of the rotor is stopped and the content in the reaction vessels and the gel card is optically detected and analyzed. The centrifugation can be continued after an optical detection and an optical analysis and these steps can be repeated again and again. Thus, it is possible to monitor the centrifugation effect on the content in the reaction vessels without unloading the gel card of the centrifuge units.

In the preferred embodiment, the light source of the camera 54 is a stroboscopic light source. The generation of flash lights with such a stroboscopic light source is synchronized with the rotation of the rotor and the gel card, respectively, so that the flash light is generated exactly when the gel card is in the field of vision of the camera 54. In the embodiment as shown in FIGS. 14 and 15, the field of vision of the camera is disposed for detecting the gel card in the lowest position. Using such a stroboscopic light source allows arranging the camera and the light source for detecting the gel card in any other rotational position, as a picture of the gel card can be taken without stopping the rotation.

Gel cards 55 consisting of a transparent plastic material are well known in the art. Preferably, gel cards are used wherein one side of the reaction vessels is colored and the other side of the reaction vessels is made of a transparent material. The color of the colored side is preferably a light color, such as white or light grey. This colored side can be embodied by a colored plastic material or a colored coating which is applied on one side of the gel card. Such a gel card is optically scanned on the transparent side, wherein the colored side provides a colored background. This colored background increases the contrast, so that a reliable optical detection is possible even if the optical power of the light source is rather weak. Such gel cards are preferably used for blood testing, in particular typing of blood. Red agglutinations of blood can be detected with a high contrast in front of a light, particularly white or grey, background. Such gel cards having a colored side form a separate inventive concept.

The fourth example shows a camera in the centrifuge for rotating gel cards. Such a camera can also be provided in a centrifuge in order to centrifuge microtiter plates. In such a centrifuge, the camera and the corresponding light source are located in the housing surrounding the rotor and arranged with its field of vision, so that the picture of the bottom of all reaction vessels is taken when the openings of the reaction vessels are directed to the shaft of the rotor.

In all the above described examples, it is common that the reaction vessel units having reaction vessels with unclosed openings can be handed over to the centrifuge in their regular position with the openings directed upwards so that liquid sample is kept safely in the reaction vessels. This makes it easy to integrate the centrifuge into automatic robots which comprise usually handling means for handling the reaction vessel units in their regular positions. In the fourth example, the gel cards can be loaded from the top into the receptacle sections of the corresponding rotors. In the first, second and third example, the microtiter plates can be handed over to the front platform. The horizontal rotation axis makes it easy to hand over the reaction vessel units in their regular positions. Furthermore, in the centrifuge according to the above described examples the reaction vessel units are always held in an exactly defined position. There is no uncontrolled degree of freedom, as it is the case in centrifuges having a swinging rotor. This defined position allows integrating further functions in the centrifuge section, such as a camera (as described above) or a pipetting means. If a picture of the reaction vessels shall be taken automatically, it is necessary that the position of the reaction vessels is exactly known, even if the reaction vessels are rotating. The centrifuge according to the present invention can be further modified if the dispensing means are provided for dispensing a liquid into the reaction vessels when the reaction vessel units are located in the rotor of the centrifuge. For example, the second embodiment can be modified in that the top portion of the jacket wall 24 is embodied as an automatic lid, wherein a dispensing bar comprising several dispensing nozzles is located above the automatic lid. This allows to dispense washing fluid into the reaction vessels without removing the reaction vessels from the rotor. The centrifuges 1 for centrifuging microtiter plates can be provided with a retractable dispensing bar which can be automatically moved in the section in between the plate tray 11 and the shaft when the plate tray is in its lowest position. Then it is possible to automatically dispense reaction solutions into the reaction vessels located in the rotor 8, which can be further processed by centrifuging the contact of the reaction vessel.

In the following, some examples of using a centrifuge according to the present invention are explained:

There is a strong need to improve the throughput in blood banks for blood typing. Usually, automatic blood typing is carried out by means of gel cards. Such gel cards can be easily optically scanned and analyzed. However, the number of reaction vessels in such gel cards is limited, as the reaction vessels are arranged linearly and not in a two-dimensional array as it is the case in microtiter plates.

A centrifuge 1 according to the second or third example can be used for blood typing by means of microtiter plates. The blood typing can be carried out by the following sequence of steps:

1. A certain amount of a gel is automatically filled into the reaction vessels of a microtiter plate by means of a dispenser.
2. The microtiter plate is placed on the front platform 4 of the centrifuge 1. The microtiter plate is loaded into the plate tray 11 of the rotor 8 by means of the loading mechanism 33. The opening 32 of the front side wall 25 is closed.
3. The microtiter plate is arranged in the rotor with its openings directed to the shaft or rotation axis, respectively. By rotating the rotor 8, the content of the reaction vessels of the microtiter plate is centrifuged so that the gel becomes free of air bubbles and settles down to the bottom of the reaction vessels very uniformly leading to the identical filling height in each reaction vessel.
4. The microtiter plate is unloaded from the rotor by means of the loading mechanism 33 and shifted onto the front platform 4.
5. Sample material, e.g. one known type of red blood cells (RBCs) and one unknown type of red blood cells and corresponding reagents are dispensed into the reaction vessels 3 carrying the gel filling.
6. The microtiter plate is automatically loaded into the rotor by means of the loading mechanism 33, wherein the opening 32 is automatically opened and closed.
7. The internal space of the centrifuge section is tempered for a certain period and a predetermined temperature so that the content of the reaction vessels of the micro-titer plate is incubated. During the incubation step, two different types of blood samples are agglutinating and, if the two blood samples are of the same type, they do not react.
8. The microtiter plate is centrifuged. If the blood samples are agglutinated they remain on the surface or upper or radial inner section of the gel. If the blood samples do not react, the blood immerses into the gel and reaches the lower or radial outer section of the gel.
9. The microtiter plate is unloaded from the rotor to the front platform by means of the loading mechanism 33, wherein the opening 32 is automatically opened.
10. The microtiter plate is put on an optical scanner. The optical scanner scans the microtiter plate with the field of vision from below and/or above. Non-reacting blood samples are detected as red spots on the bottom of the reaction vessels. The top of the gel appears to be clear. Agglutinated blood samples will show a different pattern since agglutinated RBCs will remain as a dispersed pattern on the top of the gel. It has been shown that with optical detection with a field of vision from below, the blood types A, B and O can be reliably detected and distinguished. The use of microtiter plates for blood typing improves the throughput significantly and reduces the costs in gel based blood tying by miniaturization and stronger parallelization.

This process is carried out with the centrifuge according to the second or third example. Such a centrifuge is preferably provided with a camera, so that it is not necessary to move the microtiter plate on a separate scanner.

Cellular assays also demand washing steps in a very similar way like bead assays. Cells can be fixed to the surface of microplates by centrifugation. Therefore, a hybrid system of the centrifuge according to the third example that combines centrifugation and washing in subsequent steps of a cellular assay is advantageous. The cell plate can be put onto the front platform which can be moved between an upper and a lower position. In the lower loading position the plate is loaded into the centrifuge, so that the plate is in a position that the openings of the plate are directed to the axis of the centrifuge and cells are spin down to the bottom of the plate where they can attach. Thereafter (e.g. after treatment with a drug) cells are washed in the same instrument by moving the plate to the upper loading position of the centrifuge with openings directed to the opposite of the rotor axis. The hybrid system combines different steps of a workflow in one instrument and is extremely useful for automation saving space in robotic systems.

Magnetic beads can be uniformly distributed in a solution in a reaction vessel. The magnetic forces are much stronger on the beads in the lower section than in the upper section of the reaction vessel. Therefore it can be appropriate firstly to centrifuge the reaction vessels containing the beads (centrifuging step with the openings of the reaction vessels directed radially inwardly) and afterwards to wash the beads in the centrifuge (washing step with the openings of the reaction vessels directed radially outwardly). This is particularly advantageous when a deep well microtiter plate is used, wherein the reaction vessels have a height of 10 mm or more. With this method it is possible to use small and light magnets in combination with deep wells for washing magnetic beads.

This procedure using a large collection volume is important, because the sensitive detection of virus nucleic acids in blood bank screening start with high volumes.

Some experiments using magnetic beads 59 also comprise magnets like e.g. magnetic rods 57 to collect or hold the beads (FIG. 17). One example for such an experimental setup can further comprise a kind of a protective cavity 58 for the magnetic rod in order to avoid any contact of the rod with the sample liquid/reagent/buffer etc. 60. By this the protrusion of the protective cavity can be placed within the sample liquid/reagent/buffer etc. while the magnetic rod is put inside the cavity having no contact with the liquid. Due to the magnetic forces working through the cavity the magnetic beads will be hold on the protrusion of the cavity at the opposite side of the rod.

The protrusions of the protective cavities have to be shaped in a way suitable to enter the sample liquid or at least be close enough to the beads to collect them by the magnetic forces through the cavity wall. A possible protective cavity might for example be a kind of a negative copy of the bead containing reaction vessel 3 or microplate. The protective cavity is complementary to the form of the magnetic rod so that the rod can be tightly covered by the protective cavity. If the protective cavity is put into the plate/reaction vessel containing the beads and for example a magnetic rod is put inside the vessel of the protective cavity the magnetic beads will be collected at the outside lower part of the protective cavity.

This unit comprising the protective cavity and at least one magnetic rod, can be moved wherein the magnetic beads adhere to the outer surface of the protective cavity.

This method is used to transfer the bead together with the bound material to a different plate for the next experimental step containing the respective solution. However, together with the transfer of the beads a residual amount of liquid will also be transferred from one plate to the other. In cases of experiments with several transfer steps the amount of unwanted transferred liquid can sum up to high percentages. In order to solve this problem the centrifuge according to the invention can be used. For this the protective cavity together with the magnetic rod holding the magnetic beads on the underside of the reaction vessel is transferred to a new empty plate and placed into the centrifuge according to the invention (centrifuging step with the opening of the reaction vessel directed radially inwards).

By applying the proper centrifugation speed, the residual liquid 61 is removed from the beads while the beads stay bound to the underside of the protective cavity due to magnetic forces.

The respective speed has to be adjusted depending on the employed magnets. After this step the washing plate can be discarded and the protective cavity together with the now dried beads can be transferred to the plate required for the next experimental step.

Another experimental setup for which the centrifuge according to the invention can be used is when a rod system is used to capture the target molecule (FIG. 18a-d).

Thus, a further aspect of the invention are rods used for carrying reagents. These rods can also be used in manual operation or with a robot having a gripper for gripping such rods.

Figure 18A:
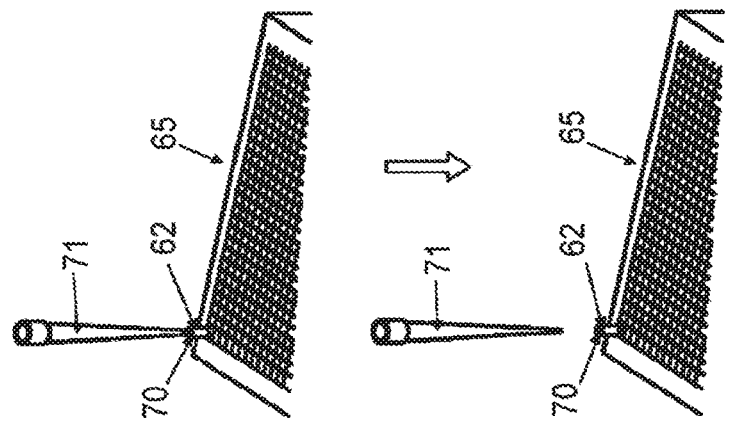

A rod system comprises rods 62 which can be magnetic or non-magnetic (FIG. 18a). The design of the rods has to be in way to meet several technical requirements.

Figure 18B:
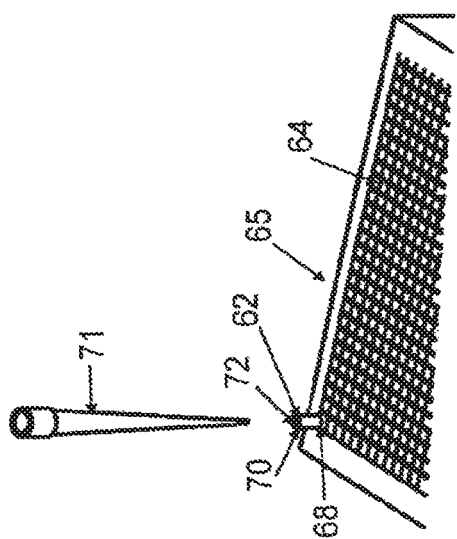
Figure 18C:
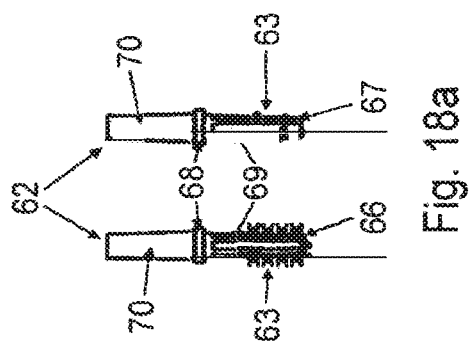

The diameter of the part of the rod, which will be placed in the reaction vessel 63, has to be adjusted to the diameter of the reaction vessel 64 (FIG. 18b). The rods can be used for either single reaction vessels or for microtiter plates 65 with 96,384 or more vessels. There for, the diameter of said rod part has to be smaller than one of the vessel but should not be too small to avoid staggering around of the rod within the vessel.

Furthermore, the rod should not have any contact with the walls of the reaction vessel since this could lead to the removal of bound antibodies 66 or antigens 67 on the rod. Therefore, the rod comprises a protrusion 68, whereby the protrusion 68 is located above the rod part being within the vessel 63. This prevents the rod from further entering into the vessel and from touching the bottom part (walls or bottom) of the vessel. Said protrusion 68 can be shaped like a ring, for example, or can just be one or more small protrusion(s).

Figure 18D:
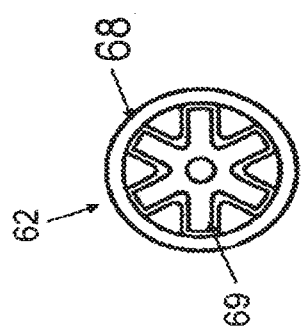

The part of the rod being placed in the vessel 63 can be shaped in any way fitting in the vessel. This can for example be cylindrical or conical. Further to increase the surface of this part of the rod it can, for example, be cross-shaped or star-shaped (FIG. 18d). Other shapes like vertical ridges or edges 69 are also suitable to increase the surface of the rod.

The lower section of the rod placed in the vessel allows the immobilization of reagents on the surface of the rod. This can be accomplished by means of surface interactions like e.g. coating or coupling. Alternatively, the rod can comprise a magnetic element, so that reagents can be immobilized via magnetic beads on the surface of the rods. This lower section is called reaction section. Thereby the rod is made of a material allowing the coupling or coating of the rod with reagents, like e.g. antibodies or antigens.

The rods for these kinds of experiments can for example comprise a magnetic element. These magnetic rods are then used to capture beads coated with, for example, antibodies. Also the direct coating of non-magnetic rods with, e.g., an antibody is possible.

In order to coat the rod with an antibody 66 or antigen 67 its surface can be modified accordingly, which is well known to a person skilled in the art.

The upper part of the rod 70, which is located above the vessel after placing the rod within the vessel, is designed in a way that it is possible to transfer the rod with a (standard) pipette tip 71 (FIG. 18c), which itself can be couple to a pipette (arm) coupling section. A preferred design comprises a blind hole 72 on top of the rod of a size that a (standard) pipette tip 71 can be put in for a few millimeters, e.g., 1 to 12 mm. Depending on the tips used (e.g. from 1000 µl to 1 µl) the tip enters the blind hole 72 with different depth. When placing the tip 71 inside of the hole by pressure, the shaft of the tip should stick stronger to the pipette itself than the tip sticks in the hole of the rod. Otherwise the tip would stay stuck in the rod.

In order to transfer the rod it is preferred that the hole is construed in shape of a tapered blind hole. Thereby, when placing the tip in the hole an airtight seal will be created by it. Once placed within the hole the pipette can generate a vacuum within the hole by sucking out the air by means of regular usage of the pipette. The vacuum will hold the rod on the pipette tip and it can be transferred to, e.g., the next reaction vessel. To release the rod the air is blown out by the regular pipette mechanism when blowing out any liquid. By reducing the vacuum the rod will then be released from the pipette tips and can e.g., slide in the reaction vessel up to the point where the protrusion 62 will hold it back.

Alternatively, the rod can be also gripped by means of a regular gripping device.

However, regular gripping devices commonly grip devices alongside. This comes along with the need of space for the gripping device for every single device to be gripped. For placing rods in every single vessel of a microplate a simultaneous gripping of rods for every vessel is barely realizable. According to the present mechanism by using the pipettes together with the tips as gripping devices as many rods can be placed in reaction wells as many pipette tips are held by the pipette device. Also single selected vessels on one plate can be used with the rod system while others are left unused.

The vessels can be filled with different sample liquids in order to perform quick testing of several samples on one plate by using rods coated with the same or different antibodies or antigens.

After coating the rods or collecting the coated beads, the rods are then placed in the reaction vessel containing the corresponding sample liquid.

When transferring the rod from one reaction vessel to the next (depending on the experiment many transfers might be required) the transfer of residual sample liquid is undesired. Therefore, the rod can be placed in an empty reaction vessel, which can be put in the centrifuge according to the present invention. By a centrifugation step with the opening of the reaction vessel directed radially inwards the unwanted residual liquid can be removed easily from the rod before transferring it to the next reaction vessel.

By this, the amount of unwanted transferred residual liquid can be reduced enormously re-suiting in improved reaction conditions.

Regular gripping devices commonly grip devices alongside. This comes along with the need of space for the gripping device for every single device to be gripped. For placing rods in every single vessel of a microplate a simultaneous gripping of rods for every vessel is barely realizable. According to the present mechanism by using the pipettes together with the tips as gripping devices as many rods can be placed in reaction wells as many pipette tips are held by the pipette device. Also single selected vessels on one plate can be used with the rod system while others are left unused.

Commonly used pipette robots can carry a maximum of 96 standard pipette tips. This number is limited due to reaction well size and the diameter of the pipette tip at its upper end where it is coupled to the pipette device. There are pipette arms carrying more than 96 tips, e.g. 384, however, these are employing special tips, which are expensive. In order to handle the rods disclosed herein in higher numbers than 96 either expensive special tips have to be employed or, since the design of these rods allows the handling with normal prized standard pipette tips and standard pipetting head with 96 channels, the rods just need to be moved four times in order to fill a complete 384 vessel plate with 384 rods. These steps, however, do not need much time and, thus, do not slow down the experimentation process in a significant manner. The rods can be moved in a staggered way to place a rod in every second vessel of a 384 plate, for example. Even the handling of more than 384 rods for plates with more vessel can be realized and only requires the adaption of the rod size in accordance with the vessel size.

The rods disclosed herein can controllable be gripped and released of the reagent carrier units with an ordinary liquid handler. Any lipid handler can be used. There is no need to mechanically adapt the liquid handler for enabling it to handle also reagent carrier units.

Devices, which are embodied for pipetting any kind of liquids are well known to a person skilled in the art. These kinds of devices are also called liquid handler. The most common liquid handlers are pipettes or robot arms for pipetting fluids.

Thus, the rods and their convenient way of handling via pipette tips allow a fast handling of high numbers of rods, which can be automated easily without additional costs for special tips or pipette devices.

Amplification reactions of nucleic acids typically require high temperatures (like PCR). They are carried out in high throughput in microtiter plates. In order to prevent evaporation of single reaction volumes plate sealers are used to fix a foil on top of the microtiter plate. It is costly and difficult to integrate plate sealers into automatic labor robotic systems. Instead of the foil mineral oil has been used to cover the reaction in the early days of PCR. A robot can easily handle the mineral oil but small quantities of aqueous solutions and small quantities of mineral oil might be difficult to be dispensed to form two separate phases (oil on top) in microtiter plates with high performance. A centrifugation step is needed to separate the phases and make 100% sure for all reactions that coverage is successful and no aqueous volume will evaporate. The centrifuge is easy to integrate in robotic workflows as described above.

LIST OF REFERENCES 1 centrifuge
2 microtiter plate
3 reaction vessel
4 front platform
5 centrifuge section
6 driving section
7 rim
8 rotor
9 housing
10 shaft
11 plate tray
12 base wall
13 U-rail
14 base shank
15 side shank
16 side shank
17 central bore
18 rotation axis
19 stopper
20 microtiter plate carrier
21 rim
22 coupling element
23 housing
24 jacket wall
25 front side wall
26 rear side wall
27 lower half shell
28 upper half shell
29 flange
30 drain
31 support
32 opening
33 loading mechanism
34 flexible elongated beam
35 inner wall
36 free end
37 upper strand
38 lower strand
39 wheel
40 wheel
41 stepper motor
42 magnetic element
43 leg
44 flange
45 counterweight
46 leg
47 motor
48 lifting means
49 dispensing bar
50 dispensing nozzle
51 centrifuge housing
52 rotor
53 lid
54 camera
55 gel card
56 rotor space
57 magnetic rod
58 protective cavity
59 magnetic beads
60 sample liquid/reagent/buffer etc.
61 residual liquid removed from cavity/beads
62 rod
63 lower part of the rod
64 reaction vessel
65 microtiter plate
66 antibody
67 antigen
68 protrusion
69 ridges/edges
70 upper part of the rod
71 schematic depiction of a pipette tip
72 blind hole

The invention claimed is:

1. A centrifuge for cleaning a reaction vessel unit with at least one opening, comprising:
a centrifuge section including a housing and a rotor disposed within the housing, wherein the rotor is configured to hold the reaction vessel unit with its at least one opening directed outwardly;
a motor for rotating the rotor around a horizontal rotation axis; and
a loading mechanism for loading and unloading the centrifuge with the reaction vessel unit, the loading mechanism including a beam and an actuator, wherein the beam is configured to couple with the reaction vessel unit and wherein the actuator is coupled with the beam to extend the beam to an extended state and to retract the beam to a retracted state, wherein the beam in the extended state extends through the centrifuge section and wherein the beam in the retracted state is removed from the centrifuge section so that the rotor can freely rotate,
wherein the rotor includes front and rear sides along the horizontal rotation axis, wherein the rear side of the rotor is disposed between the front side of the rotor and the beam in the retracted state, and wherein a stopper is provided at the rear side of the rotor.

2. The centrifuge according to claim 1, wherein the housing includes an opening at a front end for loading and unloading the centrifuge with the reaction vessel unit, wherein the opening and the actuator are arranged on opposite sides of the rotor, and wherein the beam in the extended state extends through the rotor and the opening.

3. The centrifuge according to claim 1, wherein a first magnetic element is provided at a free end of the beam to couple with the reaction vessel unit.

4. The centrifuge according to claim 3, wherein the first magnetic element is configured to couple with the reaction vessel unit via a coupling element of the reaction vessel unit or a coupling element of a reaction vessel unit carrier.

5. The centrifuge according to claim 4, wherein the first magnetic element is configured to uncouple with the reaction vessel unit when the reaction vessel unit abuts the stopper.

6. The centrifuge according to claim 4, wherein the first magnetic element is configured to uncouple with the reaction vessel unit when the reaction vessel unit carrier carrying the reaction vessel unit abuts the stopper.

7. The centrifuge according to claim 4, wherein the rotor comprises a second magnetic element configured to couple with the reaction vessel unit.

8. The centrifuge according to claim 7, wherein the stopper comprises the second magnetic element.

9. The centrifuge according to claim 8, wherein the stopper is configured to couple with the reaction vessel unit when the first magnetic element is uncoupled with the reaction vessel unit.

10. The centrifuge according to claim 9, wherein the stopper is configured to couple with the reaction vessel unit via the reaction vessel unit carrier when the first magnetic element is uncoupled with the reaction vessel unit.

11. The centrifuge according to claim 9, wherein the beam is movable along a second axis parallel to the rotation axis of the rotor, and wherein the stopper is laterally spaced from the second axis.

12. The centrifuge according to claim 1, further comprising a platform configured to support the reaction vessel unit and oriented parallel to the rotation axis of the rotor.

13. A system comprising:
a reaction vessel unit with at least one opening, the reaction vessel unit comprising a plurality of reaction vessels which are arranged in a two-dimensional array;
a centrifuge for cleaning the reaction vessel unit, comprising:
a centrifuge section including a housing and a rotor disposed within the housing, wherein the rotor is configured to hold the reaction vessel unit with its at least one opening directed outwardly;
a motor for rotating the rotor around a horizontal rotation axis; and
a loading mechanism for loading and unloading the centrifuge with the reaction vessel unit, the loading mechanism including a beam and an actuator, wherein the beam is configured to couple with the reaction vessel unit and wherein the actuator is coupled with the beam to extend the beam to an extended state and to retract the beam to a retracted state, wherein the beam in the extended state extends into the centrifuge section and wherein the beam in the retracted state is removed from the centrifuge section so that the rotor can freely rotate;
wherein a first magnetic element is provided at a free end of the beam to couple with the reaction vessel unit and is configured to couple with the reaction vessel unit via a coupling element of the reaction vessel unit or a coupling element of a reaction vessel unit carrier;
wherein the rotor includes front and rear sides along the horizontal rotation axis, wherein the rear side of the rotor is disposed between the front side of the rotor and the beam in the retracted state, and wherein a stopper is provided at a rear side of the rotor that comprises a second magnetic element configured to couple with the reaction vessel unit; wherein the stopper is configured to couple with the reaction vessel unit when the first magnetic element is uncoupled with the reaction vessel unit;
and
wherein the coupling element is configured to couple the reaction vessel unit with at least one of the first magnetic element and the second magnetic element.

14. The system according to claim 13, wherein the coupling element is part of the reaction vessel unit.

15. The system according to claim 13, wherein the coupling element is part of the reaction vessel unit carrier.

16. The system according to claim 13, wherein the coupling element comprises a plate oriented perpendicular to the rotation axis of the rotor.

17. The system according to claim 13, wherein the second magnetic element is configured to couple with the coupling element to hold the reaction vessel unit with its at least one opening directed outwardly.

18. A method of cleaning a reaction vessel unit with a centrifuge, the centrifuge comprising a centrifuge section including a housing and a rotor disposed within the housing, the method comprising:
loading the reaction vessel unit into the centrifuge section by extending a beam through the rotor, coupling the beam with the reaction vessel unit, retracting the beam to draw the reaction vessel unit into the rotor, and stopping the reaction vessel unit in the rotor via a stopper, wherein the rotor includes front and rear sides along the horizontal rotation axis, wherein the rear side of the rotor is disposed between the front side of the rotor and the beam in the retracted state, and wherein the stopper is provided at a rear side of the rotor;
uncoupling the beam from the reaction vessel unit;
coupling the reaction vessel unit with the rotor;
retracting the beam from the centrifuge section; and
centrifuging the reaction vessel unit by rotating the rotor around a horizontal rotation axis within the housing.

19. The method according to claim 18, wherein the step of stopping the reaction vessel unit is performed using the stopper that allows the beam to be retracted from the centrifuge section.

20. The method according to claim 19, wherein the beam comprises a first magnetic element and the step of coupling the beam with the reaction vessel unit is performed using the first magnetic element.

21. The method according to claim 20, wherein the stopper comprises a second magnetic element and the step of coupling the reaction vessel unit with the rotor is performed using the second magnetic element.

22. The centrifuge according to claim 1, wherein the horizontal rotation axis extends between front and rear ends of the housing, the loading mechanism is configured to load and unload the centrifuge with the reaction vessel unit via the front end of the housing, and the stopper provided at the rear side of the rotor is between the front end of the housing and the beam in the retracted state.

* * * * *